United States Patent
Kikuchi et al.

(10) Patent No.: US 10,618,954 B2
(45) Date of Patent: Apr. 14, 2020

(54) CKAP4-MOLECULAR-TARGETED ANTITUMOR AGENT

(71) Applicant: Osaka University, Suita-shi, Osaka (JP)

(72) Inventors: Akira Kikuchi, Suita (JP); Katsumi Fumoto, Suita (JP); Hirokazu Kimura, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 15/553,941

(22) PCT Filed: Jan. 28, 2016

(86) PCT No.: PCT/JP2016/052485
§ 371 (c)(1),
(2) Date: Aug. 25, 2017

(87) PCT Pub. No.: WO2016/136372
PCT Pub. Date: Sep. 1, 2016

(65) Prior Publication Data
US 2018/0037649 A1    Feb. 8, 2018

(30) Foreign Application Priority Data

Feb. 27, 2015   (JP) ................................. 2015-038343

(51) Int. Cl.
| | | |
|---|---|---|
| *A61K 48/00* | (2006.01) | |
| *C07K 16/28* | (2006.01) | |
| *A61K 49/00* | (2006.01) | |
| *A61K 31/7105* | (2006.01) | |
| *A61K 31/713* | (2006.01) | |
| *A61K 39/395* | (2006.01) | |
| *G01N 33/574* | (2006.01) | |
| *C07K 16/30* | (2006.01) | |
| *C12N 15/113* | (2010.01) | |
| *C12Q 1/6886* | (2018.01) | |
| *G01N 33/50* | (2006.01) | |

(52) U.S. Cl.
CPC ........... *C07K 16/28* (2013.01); *A61K 31/713* (2013.01); *A61K 31/7105* (2013.01); *A61K 39/395* (2013.01); *A61K 48/00* (2013.01); *A61K 49/00* (2013.01); *C07K 16/303* (2013.01); *C07K 16/3023* (2013.01); *C12N 15/1138* (2013.01); *C12Q 1/6886* (2013.01); *G01N 33/5011* (2013.01); *G01N 33/5023* (2013.01); *G01N 33/57423* (2013.01); *G01N 33/57438* (2013.01); *G01N 33/57488* (2013.01); *G01N 33/57492* (2013.01); *C07K 2317/76* (2013.01); *C12N 2310/14* (2013.01); *C12N 2310/531* (2013.01); *C12Q 2600/118* (2013.01); *C12Q 2600/136* (2013.01); *C12Q 2600/158* (2013.01); *C12Q 2600/178* (2013.01); *G01N 2333/4704* (2013.01); *G01N 2333/705* (2013.01); *G01N 2500/02* (2013.01)

(58) Field of Classification Search
None
See application file for complete search history.

(56) References Cited

U.S. PATENT DOCUMENTS

| | | | | |
|---|---|---|---|---|
| 8,962,585 B2 * | 2/2015 | Collard | ............... | A61K 31/7088 514/44 A |
| 2012/0201810 A1 | 8/2012 | Ng Liu | | |
| 2012/0295953 A1 | 11/2012 | Colalrd et al. | | |
| 2015/0126587 A1 | 5/2015 | Collard et al. | | |

FOREIGN PATENT DOCUMENTS

| | | |
|---|---|---|
| JP | 2013-515505 A | 5/2013 |
| WO | WO 2008/014484 A1 | 1/2008 |
| WO | WO 2008/144485 A2 | 11/2008 |

OTHER PUBLICATIONS

Kaba et al (Asian Pacific Journal of Cancer Prevention, 2014. vol. 15, pp. 381-384. ).*
Bir et al., "Potential utility of p63 expression in differential diagnosis of non-small-cell lung carcinoma and its effect on prognosis of the disease", Med. Sci. Monit., 2014, vol. 20, pp. 219-226.
Conrads, et al., "CKAP4/p63 Is a Receptor for the Frizzled-8 Protein-related Antiproliferative Factor from Interstitial Cystitis Patients", J. Biol. Chem., 2006, vol. 281, No. 49, pp. 37836-37843.
Li et al., "Expression of cytoskeleton associated protein 4 is related to lymphatic metastasis and indicates prognosis of intrahepatic cholangiocarcinoma patients after surgery resection", Cancer Lett., 2013, vol. 337, No. 2, pp. 248-253.
Liu, et al., "Effect of small interfering RNA targeting p63 on the proliferation and invasiveness of human cholangiocarcinoma cells in vitro", J. South. Med. University, 2012, vol. 32, No. 2 pp. 207-210.
Shi, et al. "High Expression of Dickkopf-Related Protein 1 is Related to Lymphatic Metastasis and Indicates Poor Prognosis in Intrahepatic Cholangiocarcinoma Patients After Surgery", Cancer, 2013, vol. 119, No. 5, pp. 993-1003.
Soldevilla, et al. "Tumor-derived exsosomes are enriched in deltaNp73, which promotes oncogenic potential in acceptor cells and correlates with patient survival", Hum. Mol. Genet., 2014, vol. 23, No. 2, pp. 467-478.
Yamabuki, et al., "Dikkopf-1 as a Novel Serologic and Prognostic Biomarker for Lung and Esophageal Carcinomas", Cancer Res., 2007, vol. 67, No. 6, pp. 2517-2525.
Yanagita et al., "Haigan Soshiki Kanja Kessei ni Okeru CKAP4 no Hatsugen Kento", Nippon Byori Gakkai Kaishi, 2011, vol. 100, No. 1, p. 381.

(Continued)

*Primary Examiner* — Celine X Qian
(74) *Attorney, Agent, or Firm* — Knobbe, Martens, Olson & Bear LLP

(57) ABSTRACT

Disclosed is to identify a target molecule that is involved in Dkk1-induced hyperproliferation of tumor cells to provide a novel antitumor agent. Cytoskeleton-associated protein 4 (CKAP4) specifically regulates the hyperproliferation effects that are induced by dickkopf-related protein 1 (Dkk1), and proliferation of tumor cells can be suppressed by inhibiting expression or function of CKAP4 in the tumor cells.

5 Claims, 14 Drawing Sheets

Specification includes a Sequence Listing.

(56) References Cited

OTHER PUBLICATIONS

Ye, et al., "p63 regulates growth of esophageal squamous carcinoma cells via the Akt signaling pathway", Int. J. Oncol., 2014, vol. 44, No. 6, pp. 2153-2159.
K. M. Tuffy, et al., "Cytoskeleton-Associated Protein 4: Functions Beyond the Endoplasmic Reticulum in Physiology and Disease," International Scholarly Research Network, ISRN Cell Biology, Vo. 2012, Art ID 142313—11 pages.
Y. Li et al., "Are interactions with p63 and p73 involved in mutant p53 gain of oncogenic function?," Oncogene (2007) 26, pp. 2220-2225.
P. A. J. Muller et al., "p53 mutations in cancer," Nature Cell Biology, vol. 15, No. 1, Jan. 1, 2013—7 pages.
Extended European Search Report received in connection with European Patent Application No. 16755122.5, dated Aug. 8, 2018.
Li, Y., and C. Prives, Are Interactions With p63 and p73 Involved in Mutant p53 Gain of Oncogenic Function? Oncogene 26:2220-2225, 2007.
Muller, P.A.J., and K.H. Vousden, p53 Mutations in Cancer, Nature Cell Biology 15(1):2-8, Jan. 2013.
Tuffy, K.M., and S.L. Planey, Cytoskeleton-Associated Protein 4: Functions Beyond the Endoplasmic Reticulum in Physiology and Disease, ISRN Network Cell Biology, 2012, 11 pages.
Office Action issued in Chinese Patent Application No. 201680012273.5 dated Dec. 3, 2019.
Sato, N., et al., Wnt Inhibitor Dickkopf-1 as a Target for Passive Cancer Immunotherapy, Cancer Research 70(13):5326-5336, 2010.
Takahashi, N., et al., Dickkopf-1 is Overexpressed in Human Pancreatic Ductal Adenocarcinoma Cells and is Involved in Invasive Growth, International Journal of Cancer 126:1611-1620, 2010.
Koch, K.R., The Effect of a Novel Frizzled 8-Related Antiproliferative Factor on in vitro Carcinoma and Melanoma Cell Proliferation and Invasion, Investigational New Drugs 30:1849-1864, 2012.

* cited by examiner

CKAP4-MOLECULAR-TARGETED ANTITUMOR AGENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to an antitumor agent. More specifically, the present invention relates to an antitumor agent which can target cytoskeleton-associated protein 4 (CKAP4, 63-KDa, cytoskeleton-linking membrane protein (CLIMP-63), P63, ERGIC-63)) as a target molecule and can suppress the proliferation of tumor cells through the suppression of the expression or function of CKAP4. The present invention also relates to: a method for testing to examine the postoperative prognosis in a cancer patient; and a method for testing to check on cancer.

Description of the Related Art

In the Wnt signaling pathway, a signal involved in the function of a cell is transmitted through LDL receptor-related protein 5 or 6 (LRP5/6) or seven-transmembrane receptor Frizzled upon the binding of Wnt, which is an extracellular secreted glycoprotein, to a receptor. A Wnt signal is involved in various types of cell function regulations. It is known that abnormalities in the Wnt signaling pathway can induce cancer, bone diseases, inflammations, infections and the like.

Dkk1 (Dickkopf1) is known to be a factor which can be expressed by a Wnt signal and can inhibit the binding between a Wnt ligand and LDL receptor-related protein 6 (LRP6) to regulate the Wnt signaling pathway, and Dkk1 forms a negative feedback mechanism. A Wnt signal can positively regulate the proliferation of cells. Therefore, it has been believed previously that Dkk1 can negatively regulate the proliferation of cells.

In recent years, on the other hand, it is reported that Dkk1 can enhance the proliferation of tumor cells. More specifically, Non-Patent Document 1 reports that Dkk1 is overexpressed in multiple myeloma, hepatoblastoma, Wilms tumor, prostate cancer, renal cancer, breast cancer, esophageal cancer, lung cancer and the like and the suppression of the expression of Dkk1 and an anti-Dkk1 antibody are effective for the suppression of the proliferation of tumor cells.

As mentioned above, although Dkk1 can negatively regulate the proliferation of cells in the Wnt signaling pathway, Dkk1 also has a function to enhance the proliferation of cells. Therefore, it is assumed that Dkk1 can enhance the proliferation of cells through a signaling pathway that is independent from the Wnt signaling pathway. However, a signaling pathway through which the proliferation of cells can be enhanced by Dkk1 is not clarified yet.

On the other hand, CKAP4 is a transmembrane receptor, and an anti-proliferative factor (APF), surfactant protein A (SPA), a tissue plasminogen activator (TPA) and the like are known as the ligands for CKAP4. However, it is not reported that any one of the ligands has an activity of enhancing the cell hyperproliferation through CKAP4.

SUMMARY OF THE INVENTION

Problems to be Solved by the Invention

The present inventors have established a Dkk1-expressing strain (an MDCK/Dkk1-FLAG cells) using MDCKs cell originated from a canine renal tubule, and it is confirmed that Dkk1 can enhance the proliferation ability of the MDCK cell, as demonstrated in the section "Examples" below. From these facts, it is assumed that Dkk1 can enhance the proliferation of cells through a signaling pathway that is independent from the Wnt signaling pathway.

Thus, it becomes possible to develop a novel antitumor agent if a signaling pathway through which the proliferation of tumor cells by Dkk1 can be enhanced is clarified and a target molecule involved in the proliferation of tumor cells is identified. Under these situations, one object of the present invention is to identify a target molecule that is involved in Dkk1-induced hyperproliferation of tumor cells and to provide a novel antitumor agent. Another object of the present invention is to provide a method for screening for an antitumor agent using the target molecule.

Still another object of the present invention is to provide: a test method for predicting the postoperative prognosis in a cancer patient; and a test method for predicting the presence or absence of the development of cancer.

Means for Solving the Problem

The present inventors have made intensive and extensive studies for the purpose of clarifying a signaling pathway through which the proliferation of tumor cells can be enhanced by Dkk1, and it is found that CKAP4 acts as a receptor for Dkk1 in a signaling pathway that is independent from the Wnt signaling pathway. The present inventors found that Dkk1 can enhance the proliferation of tumor cells through the association between CKAP4 and PI3K, and it is found that CKAP4 can regulate the cell hyperproliferation effect by Dkk1 specifically and is partially involved in a cell proliferation regulation mechanism that is not known in the past. The present inventors also found that the proliferation of tumor cells can be suppressed by suppressing the expression or function of CKAP4 in the tumor cells. The present invention has been accomplished by making further studies on the basis of these findings.

Namely, the present invention provides the following aspects of inventions.

An antitumor agent characterized by containing a substance capable of suppressing the expression or function of CKAP4 as an active ingredient.

The antitumor agent according to item 1, wherein the substance is at least one nucleic acid medicine selected from the group consisting of siRNA, shRNA, dsRNA, miRNA and an antisense nucleic acid each against CKAP4.

The antitumor agent according to item 1, wherein the substance is an antibody capable of binding specifically to CKAP4 or a fragment of the antibody.

The antitumor agent according to any one of items 1 to 3, wherein the antitumor agent is used for the treatment or prevention of cancer or for the prevention of the progression of cancer.

The antitumor agent according to item 4, wherein the cancer is a type of cancer in which CKAP4 is expressed.

The antitumor agent according to item 5, wherein Dkk1 is also expressed in the cancer.

The antitumor agent according to any one of items 4 to 6, wherein the cancer is lung cancer or pancreatic cancer.

A use of a substance capable of suppressing the expression or function of CKAP4 for the production of an antitumor agent.

A substance capable of suppressing the expression or function of CKAP4, which can be used for the treatment of cancer.

A method for treating cancer, comprising a step of administering a therapeutically effective amount of a substance capable of suppressing the expression or function of CKAP4 to a cancer patient.

A method for screening for an active ingredient of an antitumor agent, comprising: step 1 of measuring the ability of each of substances of interest to suppress the expression of CKAP4 or the ability of each of the substances of interest to bind to CKAP4 located on cell membranes; and step 2 of selecting, among from the substances of interest, a substance that is confirmed to have the ability to suppress the expression of CKAP4 or the ability to bind to CKAP4 located on cell membranes as a candidate for the active ingredient of the antitumor agent.

The screening method according to item 11, wherein step 1 comprises: step 1-a of bringing each of the substances of interest into contact with cells expressing CKAP4; and step 1-b of, subsequent to step 1-a, measuring the amount of CKAP4 expressed in the cells.

The screening method according to item 11, wherein step 1 comprises: step 1-i of bringing each of the substances of interest into contact with cells expressing CKAP4; and step 1-ii of, subsequent to step 1-i, confirming whether or not each of the substances is bound to CKAP4 located on cell membranes.

A method for testing to examine the postoperative prognosis in a cancer patient, comprising a step of measuring the expression of CKAP4 in a cancer tissue collected from the cancer patient.

The test method according to item 14, further comprising measuring the expression of Dkk1 in the cancer tissue.

The test method according to item 14 or 15, wherein the cancer patient is a lung patient or a pancreatic cancer patient.

A test agent for examining the postoperative prognosis in a cancer patient, comprising a reagent for detecting CKAP4.

The test agent according to item 17, further comprising a reagent for detecting Dkk1.

The test agent according to item 17 or 18, wherein the cancer patient is a lung cancer patient or a pancreatic cancer patient.

A use of a reagent for detecting CKAP4 for the production of a test agent for examining the postoperative prognosis in a cancer patient.

A reagent for detecting CKAP4, which can be used in the testing to examine the postoperative prognosis in a cancer patient.

A method for testing to check on cancer, comprising a step of measuring CKAP4 in exosomes collected from a subject.

A test agent for checking on cancer, comprising a reagent for detecting CKAP4.

A use of a reagent for detecting CKAP4 for the production of a reagent for detecting CKAP4.

A reagent for detecting CKAP4, which can be used in the testing to check on cancer.

Advantages of the Invention

The antitumor agent according to the present invention is developed on the basis of a novel finding that CKAP4 acts as a receptor for Dkk1 and Dkk1 transmits a signal capable of enhancing the proliferation of tumor cells through CKAP4. According to the present invention, it becomes possible to suppress the proliferation of tumor cells effectively by suppressing the expression or function of CKAP4 that serves as a target molecule. Actually, an in vivo tumor suppression effect of an anti-CKAP4 antibody on various types of cancer cells is confirmed.

In addition, because the expression of Dkk1 and CKAP4 is not observed in a normal epithelial cell, the antitumor agent according to the present invention has a high specificity to tumors and is therefore superior with respect to safety.

According to the screening method of the present invention, the development of an excellent anti-malignant tumor agent can be accelerated by employing CKAP4 as a target molecule and screening for a substance capable of suppressing the expression or function of CKAP4, and therefore cancer patients can get benefits.

In addition, according to the method for testing to examine the postoperative prognosis in a cancer patient of the present invention, the postoperative prognosis can be predicted with high accuracy, and therefore the method is helpful for the determination of the best therapy strategy for the prognosis in a cancer patient. According to the method for testing to check on cancer of the present invention, the presence or absence of the development of cancer can be predicted using exosomes collected from a body fluid from a subject, and therefore it becomes possible to perform the diagnosis of cancer in a low-invasive or non-invasive manner.

BRIEF DESCRIPTION OF THE DRAWINGS

FIG. 1 (b) shows the results obtained by fixing MDCK/Dkk1-FLAG cells, which were cultured on a Transwell polycarbonate filter, and then staining the cells with an anti-Dkk1 antibody (green), an anti-E-cadherin antibody (red) and DRAQ5 DNA Dye (blue).

FIG. 1 (c) shows the results of the immunostaining of a tissue section of the kidney of a mouse at embryonic day 13 (day E13), which was embedded in paraffin, with an anti-Dkk1 antibody (green) and an anti-aPKC antibody (red).

FIG. 1 (d) shows the results obtained by culturing MDCK/Dkk1-FLAG cells on a matrigel three-dimensionally for 5 days and then measuring the formed cysts and the outer diameters (which represent the sizes of cell masses) of the formed cysts.

FIG. 1 (e) shows the results of the staining of MDCK/Dkk1-FLAG cells, which was cultured three-dimensionally on a matrigel with an anti-Ki67 antibody (green), an anti-aPKC antibody (red) and DRAQ5 DNA Dye (blue).

FIG. 1 (f) represents the results obtained by culturing MDCK cells on Transwell polycarbonate filter, then adding Dkk1 to an apical side or a basal side, then culturing the cells for 24 hours, and then staining the cells with an anti-Ki67 antibody (red) and DRAQ5 DNA Dye (blue). NT: untreated.

FIG. 1 (g) shows the results obtained by culturing MDCK/Dkk1-FLAG cells two-dimensionally for 3 days and then counting the number of the cells.

FIG. 2 (b) shows the results obtained by purifying Dkk1-binding proteins and then carrying out the silver-staining of the Dkk1-binding proteins (in the left panels) and the identified binding proteins (in the right panel).

FIG. 2 (c) shows the results of the detection of CKAP4, LRP6 and Dkk1 in a lysate (Input) of control (MDCK cells), MDCK/Dkk1-FLAG cells or MDCK/Dkk1-FLAG-GPI cells and the immunoprecipitates (IP) of the lysate with an anti-FLAG antibody.

FIG. 2 (d) shows the schematic illustrations of the domain structures of Dkk1 which were used in the test (in the upper panel) and the results of the detection of CKAP4, LRP6 and Dkk1 in a lysate (Input) of each of the control (MDCK cells) and MDCK cells expressing wild-type Dkk1-FLAG (WT) or a deletion mutant Dkk1-FLAG (ΔCRD-1, ΔCRD-2) and the immunoprecipitates (IP) of the lysate with an anti-FLAG antibody (in the lower panel).

FIG. 2 (e) shows the schematic illustrations of domain structures of CKAP4 which were used in the test (in the upper panel), the results of the detection of HA and Dkk1 in a lysate (Input) of X293T/Dkk1-FLAG cells in which wild-type CKAP4-HA (WT) or a deletion mutant CKAP4-HA (ECD, ΔC1, ΔC2, ΔC3) was transiently expressed and the immunoprecipitates (IP) of the lysate with an anti-FLAG antibody (in the lower left panels), and the results of a lysate (Input) of X293T/Dkk1-FLAG cells in which wild-type CKAP4-HA (WT) or a deletion mutant CKAP4-HA (ΔLZ) was transiently expressed and the immunoprecipitates (IP) of the lysate with an anti-FLAG antibody (in the lower right panel).

FIG. 4 (b) shows the results of detection of pAKT, AKT and clathrin in a lysate of MDCK cells incubated in a preparation solution containing Dkk1.

FIG. 4 (c) shows the results of the detection of various proteins in a lysate of MDCK cells (control) or MDCK/Dkk1-FLAG cells which were transfected with control siRNA or CKAP4 siRNA.

FIG. 4 (d) shows the results of a cell proliferation assay which was carried out on MDCK cells (control) or MDCK/Dkk1-FLAG cells (Dkk1-FLAG) which were transfected with control siRNA or CKAP4 siRNA.

FIG. 5 (b) shows the results of the detection of p110α, CKAP4 and Dkk1 in the immunoprecipitates (IP) of a lysate (Input) of a control (MDCK cells) and MDCK cells (MDCK/Dkk1-FLAG) overexpressing wild-type Dkk1-FLAG(WT) with an anti-CKAP4 antibody.

FIG. 5 (c) shows the results of the detection of p85α and HA(CKAP4) in a lysate (Input) of X293T/Dkk1-FLAG cells in which CKAP4-HA or CKAP4-ECD-HA was expressed together with p85α and the immunoprecipitates (IP) of the lysate with an anti-HA antibody.

FIG. 5 (d) shows the results of the detection of FLAG (p110β) and HA(CKAP4) in a lysate (Input) of X293T/Dkk1 cells in which CKAP4-HA or CKAP4-ECD-HA was expressed together with FLAG-p110β.

FIG. 5 (e) shows the results of the detection of p85α, CKAP4 and Dkk1 in a lysate (Input) of S2-CP8 cells expressing control shRNA(Control) or Dkk1 shRNA (Dkk1) and the immunoprecipitates (IP) of the lysate with an anti-CKAP4 antibody.

FIG. 5 (f) shows the results of the detection of p110β, CKAP4 and Dkk1 in a lysate (Input) of S2-CP8 cells expressing control shRNA(Control) or Dkk1 shRNA (Dkk1) and the immunoprecipitates (IP) of the lysate with an anti-CKAP4 antibody.

FIG. 5 (g) shows the amino acid sequence for a proline-rich domain of CKAP4 (in the upper panel) and the results of the detection of p85α and HA(CKAP4) in a lysate (Input) of X293T/Dkk1-FLAG cells transfected with a gene encoding wild-type CKAP4-HA or CKAP4-HA (a PA mutant CKAP4-HA) in which a proline residue was substituted by an alanine residue and the immunoprecipitates (IP) of the lysate with an anti-HA antibody (in the lower panels).

FIG. 5 (h) shows the schematic illustration of a domain structure of p85α (in the upper panel) and the results of the detection of GFP(p85α) and CKAP4 in a lysate (Input) of X293T/Dkk1-FLAG cells transfected with a gene encoding each of wild-type p85α (WT) (GFP-WT), ΔSH3 in which a SH3 domain was deleted (GFP-ΔSH3) and ΔSH2 (GFP-ΔSH2) in which SH2 and iSH2 domains were deleted and the immunoprecipitates (IP) of the lysate with an anti-CKAP4 antibody (in the lower panels).

FIG. 7 (b) shows the results obtained by classifying pancreatic cancer tissues (n=59) extirpated from pancreatic cancer patients on the basis of the presence or absence of the expression of Dkk1 and CKAP4 and then analyzing the relationship between the days after operation and the overall survival rate.

FIG. 7 (c) shows the results obtained by classifying pancreatic cancer tissues (n=59) extirpated from pancreatic cancer patients on the basis of the presence or absence of the expression of Dkk1 and CKAP4 and then analyzing the relationship between the days after operation and the recurrence free survival rate.

FIG. 8 (b) shows the results obtained by classifying lung adenocarcinoma tissues (n=67) extirpated from lung adenocarcinoma patients on the basis of the presence or absence of the expression of Dkk1 and CKAP4 and then analyzing the relationship between the days after operation and the recurrence free survival rate.

FIG. 8 (c) shows the results of the immunostaining of lung squamous cell carcinoma tissues extirpated from lung squamous cell carcinoma patients with an anti-Dkk1 antibody or an anti-CKAP4 antibody and haematoxylin (in the left panels) and the results of the classification of lung squamous cell carcinoma tissues (n=61) extirpated from lung squamous cell carcinoma patients on the basis of the expression amounts of Dkk1 and CKAP4 (in the right panel).

FIG. 8 (d) shows the results obtained by classifying lung squamous cell carcinoma tissues (n=61) extirpated from lung squamous cell carcinoma patients on the basis of the presence or absence of the expression of Dkk1 and CKAP4 and then analyzing the relationship between the days after operation and the recurrence free survival rate.

FIG. 8 (e) shows the results of the immunostaining of lung tissues each having lung atypical adenomatous hyperplasia with an anti-Dkk1 antibody or an anti-CKAP4 antibody and haematoxylin (in the left panels) and the results of the classification of lung atypical adenomatous hyperplasia tissues (n=11) extirpated from lung atypical adenomatous hyperplasia patients on the basis of the expression amounts of Dkk1 and CKAP4 (in the right panel).

FIG. 10 (b) shows the results of the detection of various proteins in a lysate of A549 cells transfected with control shRNA, Dkk1 shRNA, or Dkk1 shRNA and Dkk1-FLAG (in the upper left panel), the results of the detection of various proteins in a lysate of A549 cells transfected with control shRNA, CKAP4 shRNA, or CKAP4 shRNA and CKAP4-HA (in the upper right panel), and the results of a cell proliferation assay on each of the cells (in the lower panel).

FIG. 10 (c) shows the results obtained by culturing S2-CP8 cells expressing control shRNA, Dkk1 shRNA, CKAP4 shRNA, Dkk1 shRNA and Dkk1-FLAG, or CKAP4 shRNA and CKAP4-HA on a matrigel three-dimensionally and then counting the number of spheroids per one field.

FIG. 10 (d) shows the results obtained by culturing A549 cells expressing control shRNA, Dkk1 shRNA, CKAP4 shRNA, Dkk1 shRNA and Dkk1-FLAG, or CKAP4 shRNA and CKAP4-HA on a matrigel three-dimensionally and then counting the number of spheroids per one field.

FIG. 11 (b) shows the results of the analysis on the change in tumor volume of a tumor xenograft during the period of 28 days after injection and the final weight of the tumor xenograft in nude mice which received the subcutaneous injection of A549 cells expressing control shRNA, CKAP4 shRNA, or CKAP4 shRNA and CKAP4-HA.

FIG. 11 (c) shows the results of the analysis on the change in tumor volume of a tumor xenograft during the period of 21 days after injection and the final weight of the tumor xenograft in nude mice which received the subcutaneous injection of S2-CP8 cells expressing control shRNA or Dkk1 shRNA.

FIG. 11 (d) shows the results of the analysis on the change in tumor volume of a tumor xenograft during the period of 28 days after injection and the final weight of the tumor xenograft in nude mice which received the subcutaneous injection of A549 cells expressing control shRNA or Dkk1 shRNA.

FIG. 12 (b) shows the results of the staining of S2-CP8 cells, which were proliferated on a collagen-coated glass slide, in an unfixed state with an anti-CKAP4 antibody (green), phalloidin (red) and DRAQ5 DNA Dye (blue).

FIG. 12 (c) shows the results obtained by mixing GST-CKAP4-ECD with an anti-CKAP4 antibody or anti-GST antibody, then adding Dkk1 to the mixture, then incubating the resultant solution and then measuring Dkk1 bound to GST-CKAP4-ECD.

FIG. 12 (d) shows the results of the detection of various proteins in a lysate of MDCK cells which were treated with nocodazole, then added with a Dkk1 or insulin in the presence of an anti-CKAP4 antibody or an anti-GST antibody and then incubated.

FIG. 12 (e) shows the results of the detection of various proteins in a lysate of S2-CP8 cells and a lysate of A549 cells each of which were added with an anti-CKAP4 antibody or an anti-GST antibody and then incubated.

FIG. 12 (f) shows the results obtained by culturing each of S2-CP8 cells and A549 cells in the presence of an anti-GST antibody or an anti-CKAP4 antibody three-dimensionally in a matrigel and then counting the number of spheroids per one field.

FIG. 12 (g) shows the results obtained by culturing S2-CP8 cells in the presence of an anti-GST antibody or an anti-CKAP4 antibody three-dimensionally in a matrigel and then counting the number of spheroids per one field.

FIG. 12 (h) shows the results of the immunostaining of cancer tissue-originated spheroids (CTOSs) of samples LC189 and LB95 with an anti-Dkk1 antibody or an anti-CKAP4 antibody and haematoxylin.

FIG. 12 (i) shows the results of a proliferation assay on CTOSs of the samples LC189 and LB95 in the presence of an anti-CKAP4 or an anti-GST antibody.

FIG. 13 (b) shows the results of the observation of nude mice which received the subcutaneous injection of A549 cells from above and the results of the observation of tumor xenografts extirpated from the nude mice (in the left panel) and the results of the measurement of the change in tumor volume of a tumor xenograft during the period of 25 days after the injection of an antibody and the final weight of the tumor xenograft (in the right panel).

DETAILED DESCRIPTION OF THE PREFERRED EMBODIMENT

Antitumor Agent

Figure 1:
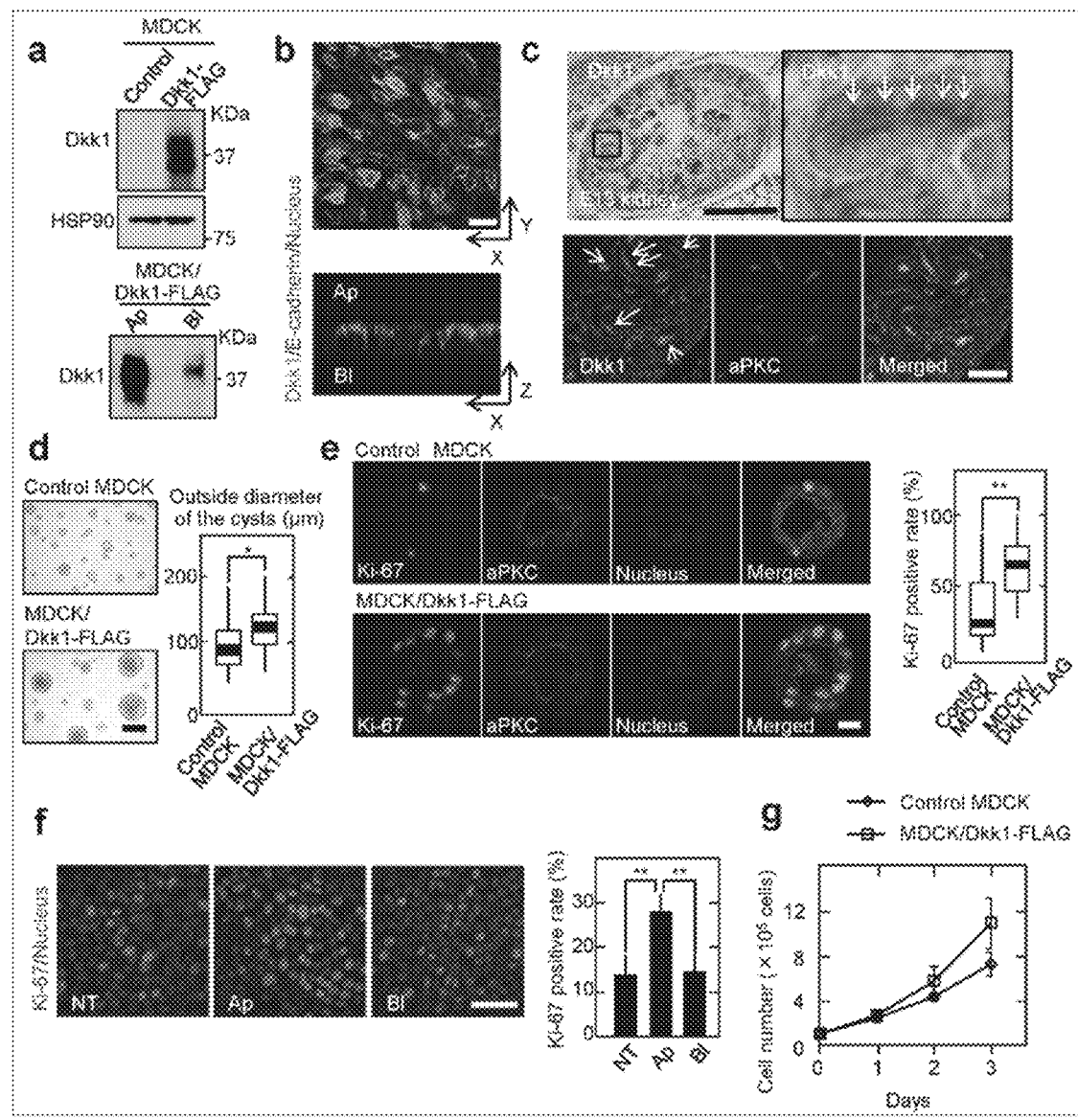
FIG. 1 (a) shows the results from which it was confirmed that Dkk1, which was tagged with FLAG at the C-terminal thereof, was expressed in MDCK cells that expressed Dkk1 gene (in the upper panels) and the result of the analysis of the expression of Dkk1 which were obtained by culturing MDCK/Dkk1-FLAG cells on a Transwell polycarbonate filter and then dividing the cells into apical side cells (Ap) and basal side cells (Bl) (in the lower panel).

The antitumor agent according to the present invention is characterized by containing a substance capable of suppressing the expression or function of CKAP4 as an active ingredient. Hereinbelow, the antitumor agent according to the present invention will be described in detail.

(Active Ingredient)

In the antitumor agent according to the present invention, a substance capable of suppressing the expression or function of CKAP4 is used as an active ingredient. CKAP4 is involved in the mechanism for the regulation of the proliferation of tumor cells as a receptor for Dkk1, and has an activity to enhance the proliferation of tumor cells. In the antitumor agent according to the present invention, it becomes possible to effectively suppress the proliferation of tumor cells by suppressing the expression or function of CKAP4.

CKAP4 is known as a transmembrane protein, and the amino acid sequence and the nucleotide sequence for CKAP4 are also known. For example, the amino acid sequence for human CKAP4 is known to be the amino acid sequence represented by SEQ ID NO: 1, and the nucleotide sequence for a gene encoding human CKAP4 is known to be the nucleotide sequence represented by SEQ ID NO: 2.

In the present invention, the "substance capable of suppressing the expression of CKAP4" is not particularly limited, as long as the substance is pharmaceutically acceptable and can suppress the expression of CKAP4 from DNA encoding CKAP4 (i.e., CKAP4 gene). The substance capable of suppressing the expression of CKAP4 may exhibit the effect to suppress the expression of CKAP4 in any stage, including a CKAP4 gene transcription stage, a CKAP4 gene post-transcriptional regulation, a CKAP4 translation stage, a CKAP4 post-translational modification stage and the like. Specific examples of the substance capable of suppressing the expression of CKAP4 include nucleic acid medicines such as: a nucleic acid molecule capable of suppressing the transcription of CKAP4 gene (e.g., a decoy nucleic acid); an RNA molecule having an RNA interference activity on mRNA for CKAP4 (e.g., siRNA, shRNA, dsRNA) or a precursor thereof; and an nucleic acid molecule capable of suppressing the transcription of mRNA for CKAP4 (e.g., miRNA, an antisense nucleic acid (antisense DNA, antisense RNA), a ribozyme). These nucleic acid medicines may be used singly, or a combination of two or more of them may be used. The nucleotide sequence for each of the nucleic acid medicines may be designed appropriately by a person skilled in the art by any know method on the basis of the information on the nucleotide sequence for CKAP4 gene. Among these nucleic acid medicines, siRNA, shRNA, dsRNA, miRNA and an antisense nucleic acid are preferred, and siRNA and shRNA are more preferred, from the viewpoint of the easiness of the application to clinical situations.

In the case where the nucleic acid molecule is an RNA molecule, the RNA molecule may be designed in such a manner that the RNA molecule can be produced in vivo. More specifically, the RNA molecule may be one in which DNA encoding the RNA molecule is inserted into an expression vector to be used in a mammalian cell. Specific examples of the expression vector include a virus vector such as a retrovirus vector, a lentivirus vector, an adenovirus vector, an adeno-associated virus vector, a herpesvirus vector and a sendai virus vector, and an animal cell expression plasmid.

The "substance capable of suppressing the function of CKAP4" is not particularly limited, as long as the substance is pharmaceutically acceptable and can suppress the function of CKAP4 located on cell membranes of tumor cells. Specific examples of the substance capable of suppressing the function of CKAP4 include an antibody capable of binding specifically to CKAP4 or a fragment of the antibody, an aptamer capable of binding specifically to CKAP4, and a low-molecular-weight compound capable of suppressing the function of CKAP4. These substances may be used singly, or two or more of them may be used. Among these substances, an antibody capable of binding specifically to CKAP4 or a fragment of the antibody is preferred.

The antibody capable of binding specifically to CKAP4 may be either one of a monoclonal antibody and a polyclonal antibody, and is preferably a monoclonal antibody. The isotype of the antibody is not particularly limited and may be any one of IgG, IgM, IgA and the like, and is preferably IgG.

In the case where the antitumor agent according to the present invention is to be administered to a human body, the antibody is preferably an antibody of which the antigenicity in a human body is decreased. More specifically, the antibody is preferably a complete human antibody, a humanized antibody, a mouse-human chimeric antibody, a chicken-human chimeric antibody or the like, and is more preferably a complete human antibody or a humanized antibody among them.

Because CKAP4 is a transmembrane protein, the antibody-binding site in CKAP4 is desirably a site in CKAP4 which is exposed on the outside of a cell (e.g., a site lying between position-128 to position-602 in SEQ ID NO: 1, preferably a site lying between position-128 to position-503 in SEQ ID NO: 1 for human CKAP4). Particularly for the binding between CKAP4 and Dkk1, a leucine zipper domain of CKAP4 (position-468 to position-503 in SEQ ID NO: 1) is needed. Therefore, the CKAP4-binding site in the antibody may be adjusted in a manner such that the binding between CKAP4 and Dkk1 in the leucine zipper domain can be suppressed.

The fragment of the antibody may be any one, as long as the fragment has at least a complementarity determination region (CDR) for specifically recognizing a target antigen and for specifically binding to the target antigen. Specific examples of the fragment include Fab, Fab', F(ab')$_2$, scFv and scFv-Fc.

The antibody and a fragment thereof can be produced in a genetically engineering manner by a conventional method.

(Diseases to be Treated)

CKAP4 is expressed in a tumor cell to enhance the proliferation of the tumor cells. According to the antitumor agent of the present invention, the proliferation of tumor cells can be suppressed by suppressing the expression or function of CKAP4. Therefore, the antitumor agent according to the present invention can be used for the treatment of cancer. The type of cancer for which the antitumor agent according to the present invention can be used is not particularly limited. Specific examples of the type of cancer include: solid cancer, such as lung cancer, pancreatic cancer, colorectal cancer, colon cancer, gastric cancer, rectal cancer, liver cancer, breast cancer, bladder cancer, prostate cancer, cervical cancer, head and neck cancer, bile duct cancer, gallbladder cancer, oral cancer, tongue cancer, pharyngeal cancer, laryngeal cancer, brain tumor, glioma, glioblastoma and multiple neural glioblastoma; and hematological cancer, such as leukemia and malignant lymphoma.

The antitumor agent according to the present invention can exert the tumor cell proliferation suppressing effect thereof effectively against a tumor cell in which CKAP4 is expressed, particularly a tumor cell in which both of CKAP4 and Dkk1 are expressed. Therefore, cancer in which CKAP4 is expressed, particularly cancer in which both of CKAP4 and Dkk1 are expressed, is a preferred disease to which the antitumor agent can be applied. Among various types of cancer, lung cancer and pancreatic cancer are particularly preferred diseases to which the anti-tumor agent according to the present invention is to be applied, because CKAP4 and Dkk1 are expressed at high frequencies in lung cancer and pancreatic cancer.

The occurrence of expression of CKAP4 in cancer can be confirmed by carrying out the tissue immunization of a collected cancer tissue. More specifically, a collected cancer tissue is immunostained with an anti-CKAP4 antibody, and it is determined that CKAP4 is expressed when a region in which the expression of CKAP4 is observed makes up 5% or more of a tumor region. A preferred example of the types of cancer to which the antitumor agent according to the present invention can apply is a type of cancer in which the CKAP4-expressed region makes up 5% or more, more preferably 20% or more, particularly preferably 50% or more, of a tumor region.

Alternatively, the occurrence of expression of CKAP4 in cancer can also be determined by collecting RNA from a collected cancer tissue and then measuring the RNA by a quantitative PCR. In this case, the determination of the presence or absence of the expression of CKAP4 may be performed employing a non-cancer tissue in the same case as a measure. More specifically, it is determined that CKAP4 is expressed in cancer when the amount of CKAP4 in a cell lysate of a cancer tissue is larger than that in a cell lysate of a non-cancer tissue in the same case.

The occurrence of expression of Dkk1 in cancer can also be confirmed by a method in which a collected cancer tissue is subjected to tissue immunization, a method in which RNA is collected from a collected cancer tissue and then the RNA is measured by a quantitative PCR and the like, as in the case of CKAP4.

More specifically, in the case where the collected cancer tissue is immunostained with an anti-Dkk1 antibody, it is determined that Dkk1 is expressed when a region in which the expression of Dkk1 is observed makes up 5% or more of a tumor region. A preferred example of the type of cancer to which the antitumor agent according to the present invention can apply is a type of cancer in which the Dkk1-expressed region makes up 5% or more, more preferably 20% or more, particularly preferably 50% or more, of a tumor region.

In the case where RNA is collected from a collected cancer tissue to measure Dkk1, it is determined that Dkk1 is expressed in cancer when the amount of Dkk1 in a cell lysate of a cancer tissue is larger than that in a cell lysate of a non-cancer tissue in the same case.

The antitumor agent according to the present invention can be used for a mammal such as bovine, pig, canine, feline, goat, rat, mouse and rabbit as well as human, and can be used suitably as a medicine for human.

(Form of Administration)

The dosage form of the antitumor agent according to the present invention may be of any one of oral administration and parenteral (non-oral) administration as long as an antitumor effect can be produced, and may be selected appropriately depending on the types of the active ingredient to be used. Specific examples of the dosage form of the antitumor agent according to the present invention include oral administration; injection administration (e.g., intravenous injection, subcutaneous injection, muscle injection, intraperitoneal injection, topical injection to an affected part); and parenteral administration such as suppository administration.

The dose amount of the antitumor agent according to the present invention may be selected appropriately depending on the types of the active ingredient to be used, the dosage form, the types of cancer to which the antitumor agent is to be applied, the levels of clinical conditions of patients and the like. For example, in the case where a nucleic acid molecule is used as the active ingredient, the nucleic acid molecule may be usually administered at a single dose of about 0.01 µg to 1000 mg/kg body weight, preferably about 0.1 to 100 µg/kg body weight. In the case where an antibody or a fragment thereof or a low-molecular-weight compound is used as the active ingredient, the substance may be usually administered at a single dose of about 0.1 mg to 20 mg/kg body weight at a frequency of about once per 1 to 3 weeks.

The antitumor agent according to the present invention may be used singly, or may be used in combination with at least one other drug having an anti-tumor effect and/or at least one radiation therapy.

(Dosage Form)

The antitumor agent according to the present invention can be prepared in a dosage form that is suitable for the types of the active ingredient and the forms of administration. Examples of the dosage form of the antitumor agent according to the present invention include: a solid preparation including tablets, capsules, pills, a powder, granules and a suppository; and a liquid preparation including a solution, a suspension, an emulsion and an injection.

The antitumor agent according to the present invention can be formulated by adding a pharmaceutically acceptable carrier and an additive, depending on the dosage form thereof. For example, in the case of a solid preparation, the solid preparation can be formulated by adding an excipient, a binder, a disintegrating agent, a lubricant and the like. In the case of a liquid preparation, the liquid preparation can be formulated by adding physiological saline, a buffer and the like.

In the antitumor agent according to the present invention, in the case where a nucleic acid molecule is used as the active ingredient, it is desirable that the antitumor agent is formulated together with a nucleic acid introduction aid so that the nucleic acid molecule can migrate into a tumor cell easily. Specific examples of the nucleic acid introduction aid include lipofectamine, oligofectamine, RNAi fect, a liposome, a polyamine, DEAE dextran, calcium phosphate and a dendrimer.

Screening Method

The screening method according to the present invention is a method for screening for an active ingredient of the antitumor agent, and is characterized by comprising: step 1 of detecting the ability of each of substances of interest (wherein the substances of interest also referred to as "test substances", hereinafter) to suppress the expression of CKAP4 or the ability of each of the test substances to bind to CKAP4 located on cell membranes; and step 2 of selecting, among from the test substances, a test substance that is confirmed to have the ability to suppress the expression of CKAP4 or the ability to bind to CKAP4 located on cell membranes as a candidate for the active ingredient of the antitumor agent. Hereinbelow, the screening method according to the present invention will be described in detail.

(Test Substance)

In the screening method according to the present invention, the test substance may be any one, as long as the test substance can be employed as a candidate substance for the active ingredient of the antitumor agent. The type of the test substance is not particularly limited, and may be, for example, a naturally occurring substance such as a biological substance or a synthetic substance that is synthesized chemically. Specific examples of the test substance include: a low-molecular-weight compound; a protein such as an antibody; and a nucleic acid molecule such as siRNA, shRNA, dsRNA, miRNA, antisense DNA, antisense RNA and an aptamer.

(First Step)

In the screening method according to the present invention, as step 1, the ability to suppress the expression of CKAP4 or the ability to bind to CKAP4 located on cell membranes is detected first.

The specific technique for detecting the ability to suppress the expression of CKAP4 of the test substance is not particularly limited, and an example of the method is a method in which step 1-a and step 1-b as mentioned below are carried out:

step 1-a: a step of bringing the test substance into contact with cells expressing CKAP4; and step 1-b: a step of, subsequent to step 1-a, measuring the amount of CKAP4 expressed in the cells.

The cell expressing CKAP4, which is to be used in step 1-a, is not particularly limited, as long as CKAP4 can be expressed in the cell. For example, a cell which can express CKAP4 endogenously (e.g., a tumor cell), a cell which is produced by transfecting CKAP4 gene into a normal cell to acquire a CKAP4-expressing ability, and the like can be used. The transfection of CKAP4 gene into a normal cell can be achieved by a known genetic engineering technique.

In step 1-a, in order to bring the test substance into contact with cells expressing CKAP4, the following process can be carried out: the cells and the test substance are added to a culture medium in which the cells can grow and then the cells are cultured at a temperature at which the cells can grow. In the case where a nucleic acid molecule such as siRNA, shRNA, dsRNA, miRNA, antisense DNA and antisense RNA is used as the test substance, it is preferred to allow a nucleic acid introduction aid to co-exist so that the nucleic acid molecule can be introduced into the cells easily. The type of the nucleic acid introduction aid is as mentioned in the section "1. Antitumor agent".

In step 1-b, the measurement of the amount of CKAP4 expressed in the cells can be achieved by measuring the amount of mRNA for CKAP4 and/or the amount of CKAP4 (the amount of a protein) by a known technique.

The concrete method for detecting the ability of the test substance to bind to CKAP4 located on cell membranes is not particularly limited, and an example of the method is a method in which step 1-i and step 1-ii as mentioned below are carried out:

step 1-i: a step of bringing the test substance into contact with cells expressing CKAP4; and step 1-ii: a step of, subsequent to the step 1-i, confirming whether or not the test substance is bound to CKAP4 located on cell membranes.

Step 1-i can be carried out by the same method as that employed in step 1-a mentioned above.

In step 1-b, the concrete technique for confirming whether or not the test substance is bound to CKAP4 located on cell membranes is not particularly limited, and the confirmation can be determined by measuring the amount of the test substance by a known immunostaining method. The confirmation can also be carried out by collecting CKAP4 from the cells subsequent to step 1-i and then measuring the amount of the test substance bound to CKAP4.

(Step 2)

In step 2, a test substance which is confirmed to have the ability to suppress the expression of CKAP4 or the ability to bind to CKAP4 located on cell membranes in step 1 as a candidate for the active ingredient of the antitumor agent.

More specifically, in the case where the ability to suppress the expression of CKAP4 is employed as a criterion of the determination, such a test substance that the expression amount of CKAP4 when step 1 is carried out with the addition of the test substance is smaller compared with the expression amount of CKAP4 when step 1 is carried out without the addition of the test substance is determined to have the ability to suppress the expression of CKAP4.

In the case where the ability to bind to CKAP4 located on cell membranes is employed as a criterion of the determination, it is determined that a test substance which is confirmed to bind to CKAP4 located on cell membranes has the ability to bind to CKAP4 located on cell membranes.

In step 2, a test substance which is confirmed to have the ability to suppress the expression of CKAP4 or the ability to suppress the binding between CKAP4 and Dkk1 is determined to have the effect to suppress the proliferation of tumor cells, and the test substance is selected as a candidate for the active ingredient of the antitumor agent. The test substance thus selected may be actually tested with respect to the effect to suppress the proliferation of tumor cells to determine whether or not the test substance can be used clinically as an antitumor agent.

Method for Testing to Examine Postoperative Prognosis in Cancer Patient

The method for testing to examine the postoperative prognosis in a cancer patient according to the present invention is characterized by comprising a step of measuring the expression of CKAP4 and Dkk1 in a cancer tissue collected from the cancer patient. According to the test method of the present invention, it becomes possible to predict the postoperative prognosis in a cancer patient by employing the expression of both of CKAP4 and Dkk1 in a cancer tissue collected from the cancer patient as a measure.

In the test method according to the present invention, the type of cancer in a patient which is to be examined in the prognosis test method is not particularly limited. Specific examples of the type of cancer include: solid cancer such as lung cancer, pancreatic cancer, colorectal cancer, colon cancer, gastric cancer, rectal cancer, liver cancer, breast cancer, bladder cancer, prostate cancer, cervical cancer, head and neck cancer, bile duct cancer, gallbladder cancer, oral cancer, tongue cancer, pharyngeal cancer, laryngeal cancer, brain tumor, glioma, glioblastoma and multiple neural glioblastoma; and hematological cancer such as leukemia and malignant lymphoma. Among these types of cancer, preferred examples of the type of cancer to be examined in the test method according to the present invention include lung cancer and pancreatic cancer.

In the test method according to the present invention, the measurement of the expression of CKAP4 in a cancer tissue collected from a cancer patient can be carried out using a reagent capable of detecting CKAP4.

An example of the method for measuring the expression of CKAP4 is a method in which a collected cancer tissue is immunostained using an anti-CKAP4 antibody. More specifically, a collected cancer tissue is immunostained using an anti-CKAP4 antibody, and it is determined that CKAP4 is expressed when a region in which the expression of CKAP4 is observed makes up 5% or more of a tumor region.

The measurement of the expression of CKAP4 can also be carried out by, for example, collecting RNA from a collected cancer tissue and then carrying out a quantitative PCR. In this case, the determination on the presence or absence of the expression of CKAP4 may be performed by employing a value in a non-cancer tissue in the same case as a reference. More specifically, it is determined that CKAP4 is expressed in cancer when the amount of CKAP4 in a cell lysate of a cancer tissue is larger than that in a cell lysate of a non-cancer tissue in the same case.

In the test method according to the present invention, from the viewpoint of the further improvement in the accuracy of prediction of the postoperative prognosis in a patient, it is desirable to also measure the expression of Dkk1 in a cancer tissue collected from the cancer patient. The measurement of the expression of Dkk1 in a cancer tissue collected from the cancer patient can be carried out using a reagent capable of detecting Dkk1.

With respect to the measurement of the expression of Dkk1, the expression can be confirmed by a method in which a collected cancer tissue is tissue-immunized, a method in which RNA is collected from a collected cancer tissue and then a quantitative PCR is carried out, and the like, as is in the case of the measurement of the expression of CKAP4.

More specifically, in the case where a collected cancer tissue is immunostained using an anti-Dkk1 antibody, it is determined that Dkk1 is expressed in the cancer when a region in which the expression of Dkk1 is observed makes up 5% or more of a tumor region. In the case where RNA is collected from a collected cancer tissue to measure Dkk1, it is determined that Dkk1 is expressed in the cancer when the amount of Dkk1 in a cell lysate of a cancer tissue is larger than that in a cell lysate of a non-cancer tissue in the same case.

In the test method according to the present invention, a cancer patient in whom the expression of both of CKAP4 and Dkk1 is observed is predicted as a patient whose postoperative prognosis is poor, namely whose overall survival period is short or relapse-free survival period is short or the like.

The present invention further provides a reagent for detecting CKAP4 in a cancer tissue, as a test kit for the above-mentioned test method. The reagent for detecting CKAP4 is not particularly limited, and examples of the reagent include an anti-CKAP4 antibody and a fragment thereof. In the test kit according to the present invention, a reagent for detecting Dkk1 in a cancer tissue may also be included. If necessary, the antibody may be labeled with biotin, a fluorescent label, a magnetic bead or the like.

Method for Testing to Check on Cancer

The method for testing to check on cancer according to the present invention is characterized by comprising a step of measuring CKAP4 in exosomes collected from a subject. According to the present invention, it becomes possible to diagnose whether or not a subject is suffering from cancer by employing the presence or absence of CKAP4 in exosomes collected from the subject as a measure.

In the test method according to the present invention, the type of cancer to be tested is not particularly limited, and specific examples of the type of cancer include: solid cancer such as lung cancer, pancreatic cancer, colorectal cancer, colon cancer, gastric cancer, rectal cancer, liver cancer, breast cancer, bladder cancer, prostate cancer, cervical cancer, head and neck cancer, bile duct cancer, gallbladder cancer, oral cancer, tongue cancer, pharyngeal cancer, laryngeal cancer, brain tumor, glioma, glioblastoma and multiple neural glioblastoma; and hematological cancer such as leukemia and malignant lymphoma. Among these types of cancer, preferred examples of the type of cancer to be examined by the test method according to the present invention include lung cancer and pancreatic cancer.

In the test method according to the present invention, the origin of the exosomes is not particularly limited, and examples of the origin include body fluids including serum and urine. Among these body fluids, serum is preferred.

The method for collecting exosomes from a subject is not particularly limited, as long as exosomes that can be used as a sample for the detection of CKAP4 can be obtained. The method may be selected appropriately among from the conventional known methods. The separation of exosomes can be carried out by an ultracentrifugation treatment. The separation of exosomes can be carried out more simply by using a commercially available kit. Specific examples of the commercially available exosome separation kit include an ExoQuick™ Exosome precipitation solution and Exoquick-TC (both manufactured by System Biosciences).

CKAP4 in exosomes can be detected by eluting a protein from the exosomes and then detecting CKAP4 using a reagent for detecting CKAP4 such as an anti-CKAP4 antibody.

In the test method according to the present invention, it is predicted that a subject has a high possibility of being suffering from cancer when the presence of CKAP4 is observed in the exosomes.

The present invention further provides a reagent for detecting CKAP4 in exosomes, as a test kit for carrying out the above-mentioned test method. The reagent for detecting CKAP4 is not particularly limited, and examples of the reagent include an anti-CKAP4 antibody and a fragment thereof. If necessary, the anti-CKAP4 antibody may be labeled with biotin, a fluorescent label, a magnetic bead or the like. In the test kit according to the present invention, a reagent for separating exosomes from a body fluid or the like may be further included.

EXAMPLES

Hereinbelow, the present invention will be described in detail on the basis of experimental data. However, the present invention is not limited by the experimental data.

In the following statements, a transfected cell is sometimes referred to as a "X/Y cell" (e.g., a MDCK/Dkk1-FLAG-GPI cell). This cell is a cell produced by transfecting an X cell with DNA encoding a protein Y. A protein is sometimes referred to as "A-B" (e.g., Dkk1-FLAG). This protein is a protein produced by fusing a peptide A to a peptide B (e.g., a tag). Transfected cells other than those produce by the production method mentioned below were produced by a method similar to the below-mentioned production method or a known genetic engineering technique.

Test Method 1-1. Separation of Protein Capable of Binding to Dkk1

A lentivirus vector harboring Dkk1 gene (Dkk1-FLAG-GPI), into which a FLAG epitope and a glycosylphosphatidylinositol (GPI) anchor signal sequence were inserted tandemly into the C-terminal side, was constructed.

MDCK cells, which are normal cells originated from a canine renal tubule, were transfected with this vector, and MDCK cells each of which was transfected with human Dkk1 gene (Dkk1-FLAG-GPI; the nucleotide sequence for human Dkk1 is represented by SEQ ID NO: 3 and the nucleotide sequence for Dkk1-FLAG-GPI is represented by SEQ ID NO: 4) (i.e., MDCK/Dkk1-FLAG-GPI cells) were selected in Dulbecco's modified Eagle's medium (DMEM) supplemented with 10 µg/ml of blasticidin S. Each of three 10-cm culture dishes containing confluent MDCK/Dkk1-FLAG-GPI cells was added with 0.5 mg/ml of sulfo-NHS-LC-biotin, and the culture dishes were incubated for 30 minutes at 4° C. and then washed with 5 ml of 1×PBS containing 50 mM of $NH_4Cl$ three times. Subsequently, cells were collected and then lysed using 1 ml of NP40 buffer (20 mM Tris-HCl, pH 8.0, 10% Glycerol, 137 mM NaCl, and 1% NP40) containing a protease inhibitor (10 g/ml Leupeptin or Aprotinin, or 1 mM PMSF).

Subsequently, centrifugation was carried out for 10 minutes, then 20 µl of a 50% slurry of protein G Sepharose beads was added to 1 ml of a collected supernatant, and then the resultant mixture was shaken for 30 minutes at 4° C. Subsequently, an anti-Flag antibody (NOVUS) was added to the resultant solution, then the solution was shaken for 30 minutes at 4° C., then a 40 µl of a 50% slurry of protein G Sepharose beads was further added to the solution, and then the resultant solution was shaken for 1 hour at 4° C. Subsequently, the beads were washed with 1 ml of NP40 buffer three times and then further washed with TBS (25 mM Tris-HCl, pH 7.4, 150 mM NaCl) three times. The collected beads were eluted by carrying out 30-minute incubation three times at 4° C. with TBS (50 µl) containing 0.2 mg/ml of Flag peptide. An eluted sample (up to 150 µl) was added with 40 µl of a 50% slurry of NeutrAvidin beads, and the resultant solution was incubated for 2 hours at 4° C. while shaking. The beads were washed twice with 1 ml of NP40 buffer and further washed once with 1 ml of 10 mM Tris-HCl (pH 7.5), and a Dkk1-bound complex was eluted with 20 µl of laemli sample buffer. Subsequently, a protein that was bound to Dkk1 was detected by protein silver staining. Seventeen bands (arrowheads in FIG. 2 (b)) were cut from the gel and then analyzed by mass spectrometry.

1-2. Polarized Secretion of Dkk1

MDCK cells ($2×10^5$ cells) expressing Dkk1 were seeded on a Transwell polycarbonate filter (Corning Costar Quality Biological, Gaithersburg, Md., USA). After 48 hours, the culture medium was replaced and then further cultured for 24 hour. In order to detect Dkk1 secreted in the culture medium, Blue Sepharose was added to each of culture media respectively collected from the apical side and the basolateral side, and the resultant solutions were incubated for 2 hours at 4° C. and then subjected to centrifugation. Precipitates were collected, and Dkk1 was detected with an anti-Dkk1 antibody.

1-3. Cell Lines and Cell Culture

MDCK type I (MDCK I) renal tubule cells were kindly provided by Dr. S. Tsukita (Osaka University, Japan), A549 and NCI-H1579 human lung adenocarcinoma cells were kindly provided by Dr. Y. Shintani (Osaka University, Japan), HeLaS3 human cervical cancer cells were kindly provided by Dr. K. Matsumoto (Nagoya University, Japan), AGS human gastric cancer cells were kindly provided by Dr. M. Hatakeyama (Tokyo University, Japan), KKLS was kindly provided by Dr. W. Yasui (Hiroshima University, Japan), HepG2 human hepatoblastoma cells were kindly provided by Dr. Y. Matsuura (Osaka University, Japan), and A549 and Calu-6 human lung adenocarcinoma cells and KYSE-70 and TE-11 human esophageal squamous cell carcinoma cells were kindly provided by Shionogi & Co., Ltd. S2-CP8 and SUIT-2 pancreatic cancer cells were purchased from Cell Resource Center for Biomedical Research, Institute of Development, Aging and Cancer Tohoku University. X293T cells were purchased from Takara Bio Inc.

All of these cell lines were cultured in Dulbecco's modified Eagle's medium (DMEM) supplemented with 10% of fetal bovine serum (FBS) or RPMI-1640. The cells expressing cDNA or shRNA which were used in this study were maintained in DMEM supplemented with 10% of FBS and 10 µg/ml of blasticidin or 800 µg/ml of G418 (geneticin).

1-4. Antibodies

The antibodies used in this test are shown in Table 1 below.

TABLE 1

| Manufacturers | Product names | Use applications |
|---|---|---|
| BD Biosciences | Anti-heat shock protein 90 (HSP90) | IB |
|  | Anti-clathrin | IB |
| Cell Signaling Technology | Anti-Ki-67 | IF |
|  | Anti-LRP6 | IB |
|  | Anti-pAKT (S473) | IB |
|  | Anti-AKT | IB |
|  | Anti-pErk1/2 | IB |
|  | Anti-Erk1/2 | IB |
|  | Anti-p-SAPK/JNK (T183/Y185) | IB |
|  | Anti-SAPK/JNK (T183/Y185) | IB |
|  | Anti-pSrc family (Tyr416) | IB |
|  | Anti-Src | IB |
|  | Anti-p110β | IB |
| Enzo Life Science | Anti-CKAP4 | IB, IP, IF, IHC |
| Novus | Anti-Flag | IB, IP |
| Santa Cruz Biothchnology | Anti-HA (Y-11) | IB, IP |
|  | Anti-PKCζ (C-20) | IF |
| R & D systems | Anti-Dkk1 | IB, IF, IHC |
| ROCKLAND | Anti-pAKT (S473) | IHC |

IB: immunoblotting
IP: immunoprecipitate
IF: immunofluorescence
IHC: immunohistochemistry 1-5. Cell Proliferation Assay Each of MDCK I cells, S2-CP8 cells and A549 cells were seeded at a density of $1×10^5$ cells/ml in a 35-mm dish. MDCK I cells were cultured in DMEM supplemented with 10% of FBS, and the other cells were cultured in DMEM supplemented with 1% of FBS. The number of cells was counted after a lapse of a predetermined number of days.

1-6. Three-Dimensional Culture of MDCK I Cells, S2-CP8 Cells and A549 Cells

The test by three-dimensional culture was carried out as previously reported (Matsumoto et al., EMBO J, 2014). In order to analyze the cyst formation of MDCK I cells and the proliferation of S2-CP8 cells and A549 cells on a matrigel (BD Biosciences, San Jose, Calif., USA), 40 µl of a matrigel was mounted on a round glass slide and then incubated for 30 minutes at 37° C. to solidify the gel. Subsequently, MDCK I cells (3×10⁴ cells) suspended in DMEM containing 10% of FBS and 2% of the matrigel and S2-CP8 cells (2×10⁴ cells) or A549 cells (2×10⁴ cells) suspended in DMEM containing 0.1% of bovine serum albumin and 2% of the matrigel were added on the solidified matrigel and then cultured.

1-7. Cancer Xenograft Analysis

The tumor xenograft analysis was carried out by a previously reported technique (Fujii et al., Oncogene, 2014) with modification. Six-week-old male BALB/cAnNCrj-nu nude mice (Charles River Laboratory Japan Inc, Osaka, Japan) were anesthetized with a combination of medetomidine (0.3 mg/kg body weight) and midazolam (4 mg/kg body weight), and then S2-CP8 cells (5×10⁶ cells) or A549 cells (5×10⁶ cells) suspended in 100 µl of phosphate buffered saline (PBS) were injected subcutaneously to the mice. Subsequently, the nude mice were subjected to analysis 21 days after the transplantation (for S2-CP8 cells) or 28 days after the transplantation (for A549 cells).

In order to assess the effects of antibodies, the nude mice were divided into two groups at the time point at which the average tumor size reached to 50 mm³. An anti-pCKAP4 antibody (150 µg/body) or an anti-glutathione-S-transferase (GST) antibody (150 µg/body) was injected into the intraperitoneal cavity for 2 weeks (on days 0, 4, 8, 12) (for S2-CP8 cells) or 3.5 weeks (on days 0, 4, 9, 12, 16, 18, 22) (for A549 cells) at a frequency of twice per week. The nude mice were subjected to analysis on day 14 (for S2-CP8 cells) or day 25 (for A549 cells) after the administration of each of the antibodies.

The volume and weight of a tumor xenograft formed at the transplanted site were measured, and the tumor xenograft was further subjected to an immunohistochemical analyses. The tumor volume was calculated in accordance with the formula: (major axis)×(minor axis)×(minor axis)×0.5. All of the animal experiments carried in this study were approved by the Animal Research Committee of Osaka University, Japan (No. 21-048-1).

1-8. Knockdown of Protein Expression by siRNA

In this experiment, the types of proteins that were targets of knockdown and the target sequences in the proteins are shown in Table 2. Cells were transfected with a mixture of siRNA molecules (20 nM each) respectively for the target proteins using RNAiMAX (Invitrogen, Carlsbad, Calif., USA). The cells obtained 36 to 48 hours after the transfection were used for the test.

TABLE 2

| siRNA | Target sequences |
|---|---|
| Randomized control | CAGTCGCGTTTGCGACTGG (SEQ ID NO: 5) |
| dog CKAP4 | GCAGAAGGTGCAGTCTCTT (SEQ ID NO: 6) |

1-9. Construction of Plasmid

FLAG-p110α and FLAG-p110β in pcDNA3mycTEVflag and p85α in pCAGGS were kindly provided by Dr. T. Asano (Hiroshima University, Japan). CKAP4 cDNA was amplified from an A549 cDNA library, and all mutants were produced by a standard technique. A lentivirus vector was constructed by inserting cDNA into CSII-CMV-MCS-IRES2-Bsd that was kindly provided by Dr. H. Miyoshi (RIKEN BioResource Center, Ibaraki, Japan). A lentivirus vector harboring shRNA was constructed by cloning an oligo DNA fragment containing a H1 promoter and shRNA into CS-RfA-EVBsd using Gateway technology (Invitrogen). The target proteins for shRNA and the target sequences in the target proteins used in this test are shown in Table 3.

TABLE 3

| ShRNA | Target sequences |
|---|---|
| luciferase | GTGCGTTGCTAGTACCAAC (SEQ ID NO: 7) |
| human Dkk1 | GGGTTTCTTGGAATGACGA (SEQ ID NO: 8) |
| human CKAP4 | GCAGATTAACCTCAGAAAT (SEQ ID NO: 9) |

1-10. Amplification of Lentivirus and Preparation of Stable Transfectants

X293T cells were transfected with each of packaging vectors (pCAG-HIV-gp and pCMV-VSV-G-RSV-Rev) and the lentivirus vector using a FuGENE HD transfection reagent (Roche Applied Science, Basel, Switzerland) to amplifying the lentivirus. The lentivirus was introduced into parental cells (5×10⁴ cells/well in a 12-well plate) in the presence of a conditioned medium and 10 µg/mL of polybrene. The cells were centrifugated at 1200×g for 1 hour, and then further incubated for another 24 hours to produce MDCK I cells, S2-CP8 cells and A549 cells each of which expressed Dkk1-Flag, CKAP4-HA, Dkk1 shRNA or CKAP4 shRNA stably.

1-11. Immunocytochemical Analysis

The cells were seeded on a glass slide and then fixed with 4% of paraformaldehyde for 20 minutes at room temperature. Subsequently, the cells were washed three times with PBS, and then blocked for 20 minutes with PBS containing 1% of BSA and 0.05% of Tween-20. Subsequently, a primary antibody was added to the solution, and the resultant solution was incubated overnight. After the cells were washed three times with PBS, a fluorescently labeling secondary antibody was added to the solution, and the resultant solution was incubated for 1 hour at room temperature. Subsequently, the glass slide was washed extensively with PBS and then sealed with PBS containing 50% of glycerol. The operations and measurements in this test were carried out using LSM510 system (Carl Zeiss Microscopy Co., Ltd, Jena, Germany).

1-12. Patients and Cancer Tissues

The experiments were carried out using tumor tissue sections (specimens) resected from pancreatic cancer patients (n=59), lung adenocarcinoma patients (n=67), lung squamous cell carcinoma patients (n=61) and lung atypical adenomatous hyperplasia patients (n=11) who underwent a surgical treatment at Osaka University Hospital in Japan during the period from April 2001 to April 2015. All of the patients were patients who did not receive any chemotherapy or radiation therapy against tumor lesions before the surgery. The ages of the pancreatic cancer patients ranged from 47 to 83 years (median, 70 years). The ages of the lung adenocarcinoma patients ranged from 39 to 85 years (median, 68 years). The ages of the lung squamous cell carcinoma patients ranged from 38 to 82 years (median, 71 years). The ages of the lung atypical adenomatous hyperplasia patients ranged from 58 to 78 years (median, 67 years).

Each of the resected specimens was observed with a microscope to measure the location and size of a tumor, each of the specimens was fixed in 10 vol % of formalin to prepare a paraffin-embedded block, and then the paraffin-embedded block was analyzed histologically. Each of the specimens used in the experiment was sectioned at a thickness of 4 μm and then stained with hematoxylin and eosin (H&E) or immunoperoxidase for the individual analyses. The protocol for this study was approved by the ethical review board of the Graduate School of Medicine, Osaka University, Japan (No. 13455).

1-13. Immunohistochemical Analysis of Dkk1, CKAP4 and pAKT in Pancreatic Cancer, Lung Adenocarcinoma, Lung Squamous Cell Carcinoma and Lung Atypical Adenomatous Hyperplasia Tissues The immunohistochemical analysis was carried out by a previously reported technique (Fujii et al., Oncogene, 2014) with modification. The concrete procedure was briefly as follows. First, all tissue sections were stained using Dako-Real™ EnVision™ Detection System (Dako, Carpentaria, Calif., USA) in accordance with the manufacturer's recommendations. More specifically, antigens were activated using Pascal pressure chamber (Dako), and then Dako REAL Peroxidase-Blocking Solution was reacted for 5 minutes to block a non-specific binding site. Subsequently, the tissue sections were treated with an anti-Dkk1 antibody (1:100), an anti-CKAP4 antibody (1:100) or a pAKT antibody (1:50) for 16 hours at 4° C. Subsequently, goat anti-mouse IgG labeled with horseradish peroxidase (HRP) was added to each of the tissue sections, then the tissue sections were incubated for 1 hour, and then diaminobenzidine (DAB) (Dako) was added to the resultant solutions. Subsequently, the tissue sections were counterstained with 0.1% (w/v) of hematoxylin. A tumor in which more than 5% of the whole area was stained was classified as being "Dkk1-positive" or "CKAP4-positive".

1-14. Statistical Analyses

The statistical analyses were carried out using JMP software (SAS Institute. Inc., Cary N.C., USA). In the examination of the postoperative relapse-free survival period and the overall survival period, differences in results were determined by a Kaplan-Meier method employing a log-rank test. With respect to the correlation between Dkk1, CKAP4 and the expression of Dkk1 and CKAP4, the correlation between tests was calculated by Monte-Carlo simulation, a multiple correction factor was calculated with taking the correlation between the tests into consideration, and the original P value was multiplied by a multiple correction factor to adapt to multiplication. Another test, i.e., Student's t-test or Mann-Whitney U-test, was employed to verify statistical significance. When a P value was less than 0.05, it was determined that there was a statistically significant difference.

2. Results of Tests 2-1. Influence of Dkk1 on Proliferation Ability of Cell

In the upper panels in FIG. 1 (*a*), the results from which it was confirmed that Dkk1, which was tagged with FLAG at the C-terminal thereof, was expressed in MDCK cells that expressed Dkk1 gene (Dkk1-FLAG) are shown. The "control" shown in FIG. 1 (*a*) was the results obtained using MDCK cells that were parental cells. HSP90 was used as a loading control. In the lower panel in FIG. 1 (*a*), the result of the analysis of the expression of Dkk1 which were obtained by culturing MDCK/Dkk1-FLAG cells cultured on a Transwell polycarbonate filter to establish apico-basal polarity and then dividing the cells into apical side cells and basal side cells is shown. In the lower panel in FIG. 1 (*a*), "Ap" represents an apical side and "Bl" represents a basal side. From these results, it was confirmed that, in MDCK cells each transfected with Dkk1 gene (Dkk1-FLAG) (MDCK/Dkk1-FLAG cells), Dkk1 that was tagged with FLAG at the C-terminal thereof was stably expressed and Dkk1-FLAG was secreted in an apical side-significant manner in the polarized MDCK cells.

In FIG. 1 (*b*), the results of the staining of the MDCK/Dkk1-FLAG cells, which were fixed on a Transwell polycarbonate filter, with each of an anti-Dkk1 antibody (green), an anti-E-cadherin antibody (red) and DRAQ5 DNA Dye (blue) are shown. E-cadherin was used as a maker for a basolateral membrane. In FIG. 1 (*b*), "Ap" represents an apical side, "Bl" represents a basal side, and the scale bar indicates 20 μm. From these results, it was confirmed that Dkk1-FLAG was localized in an apical membrane in the MDCK/Dkk1-FLAG cells.

In FIG. 1 (*c*), the results of the immunostaining of a tissue section of the kidney of a mouse at embryonic day 13 (day E13), which was embedded in paraffin, with an anti-Dkk1 antibody. The upper right panel in FIG. 1 (*c*) is an enlarged image of a region boxed in the upper left panel. The scale bar shown in the upper right panel in FIG. 1 (*c*) indicates 100 μm. In the lower panels in FIG. 1 (*c*), the results of the immunostaining of the tissue section with an anti-Dkk1 antibody (green) and an anti-aPKC antibody (red). aPKC is a marker for an apical membrane. The white arrowheads in FIG. 1 (*c*) indicate the presence of Dkk1 localized in the apical membrane. The scale bar in the lower panel in FIG. 1 (*c*) indicates 20 μm. From these results, it was found that Dkk1 was expressed in an apical side of the urinary duct of fetus kidney.

The MDCK/Dkk1-FLAG cells were cultured on a matrigel three-dimensionally for 5 days. As a control, wild-type MDCK cells were used. The outer diameters of the formed cysts were measured (n=50). The results are shown in FIG. 1 (*d*). The cysts cultured on a matrigel three-dimensionally were fixed and then the cysts were stained with an anti-Ki67 antibody (green), an anti-aPKC antibody (red) and DRAQ5 DNA Dye (blue). The results are shown in FIG. 1 (*e*). The percentage of Ki67-positive cases was calculated as the ratio of the number of Ki67-stained cells to the number of DRAQ5-stained cells in the individual cysts (n=50). In FIGS. 1 (*d*) and (*e*), the median is represented with a bold line, the box represents the $25^{th}$-$75^{th}$ percentile range, the error bars represent the $5^{th}$-$95^{th}$ percentile ranges, * represents P<0.05; ** represents P<0.01, the scale bar in (d) indicates 100 μm, and the scale bar in (e) indicates 20 μm. From these results, it was confirmed that the MDCK/Dkk1-FLAG cells had an improved proliferation ability compared with MDCK cells and Dkk1 enhanced the proliferation ability of cells.

MDCK cells were cultured two-dimensionally on Transwell polycarbonate filter for 5 days, then 250 ng/ml of Dkk1 was added to an apical side or a basal side, and then the cells were cultured for 24 hours. Subsequently, the cells were fixed and then stained with an anti-Ki67 antibody (red) and DRAQ5 DNA Dye (blue). The results are shown in FIG. 1 (*f*). The percentage of Ki67-positive cases was calculated as the ratio of the number of anti-Ki67 antibody-stained cells to the number of nuclear-stained cells (in 5 fields). Each of the results is expressed in an average value±s. d. of the results of the three independent tests. In FIG. 1 (*f*), NT represents a case where Dkk1 was not added, AP represent a case where Dkk1 was added to the apical side, Bl represents a case where Dkk1 was added to the basal side, ** represents P<0.01, and the scale bar indicates 20 μm. From the results, it was found that the expression amount of Ki67, which was a cell proliferation marker, was increased by the addition of Dkk1 and the expression amount of Ki67 was significantly increased when Dkk1 was added to the apical side. Namely, it was suggested that there was a possibility that a receptor on which Dkk1 can act is present in the apical side.

The MDCK/Dkk1-FLAG cells were cultured two-dimensionally for 3 days, and then the number of the cells was counted. The results are shown in FIG. 1 (g). As a control, MDCK cells were used. From the results, it was also confirmed that the MDCK/Dkk1-FLAG cells showed a higher proliferation ability compared with the control and Dkk1 enhanced the proliferation of cells.

2-2. Identification of Proteins Capable of Binding to Dkk1

Figure 2:
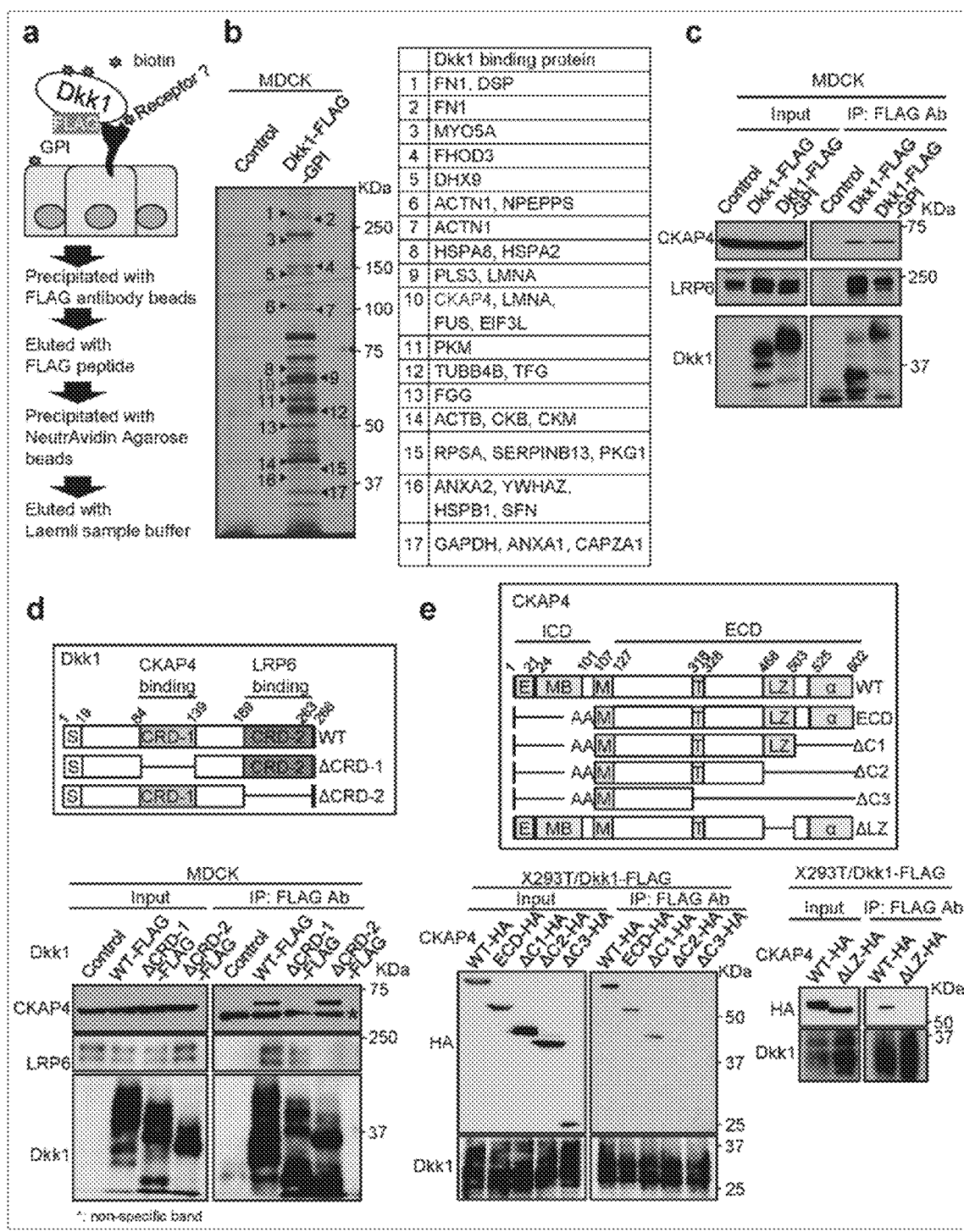
FIG. 2 (a) shows the schematic illustration of the experimental procedure for screening for Dkk1-binding proteins located on an apical side surface.

The schematic illustration of the experimental procedure for screening for Dkk1-binding proteins located on an apical side surface is shown in FIG. 2 (a). The results of silver staining of the Dkk1-binding proteins after purification of the Dkk1-binding proteins are shown in FIG. 2 (b). Seventeen bands eluted as proteins capable of binding to Dkk1-FLAG-GPI were subjected to mass spectrometry. As a result, proteins shown in the table in the right-side table in FIG. 2 (b) were detected. Among these proteins, CKAP4 was detected as band 10.

A lysate (Input) of the control (wild-type MDCK cells), MDCK/Dkk1-FLAG cells or MDCK/Dkk1-FLAG-GPI cells was immunoprecipitated with an anti-FLAG antibody. Subsequently, the lysate (Input) and the immunoprecipitates (IP) were subjected to the detection of CKAP4, LRP6 or Dkk1 using an anti-CKAP4 antibody, an anti-LRP6 antibody or an anti-Dkk1 antibody, respectively. The results are shown in FIG. 2 (c). LRP6 is a known Dkk1-binding protein and is used as a positive control. From the results, it was found that, like LRP6, CKAP4 can also form a complex with Dkk1, and an unprecedented novel finding that CKAP4 was a Dkk1-binding protein was obtained.

In the upper panel in FIG. 2 (d), the schematic illustrations of the domain structures of Dkk1 which were used in this test are shown. In the upper panel in FIG. 2 (d), S represents a signal peptide domain.

A lysate (Input) of each of the control (MDCK cells) and MDCK cells that expressed wild-type Dkk1-FLAG (WT) or a deletion mutant Dkk1-FLAG (ΔCRD-1, ΔCRD-2) was immunoprecipitated with an anti-FLAG antibody. Subsequently, the cell lysate (Input) and the immunoprecipitates (IP) were subjected to the detection of CKAP4, LRP6 or Dkk1 using an anti-CKAP4 antibody, an anti-LRP6 antibody or an anti-Dkk1 antibody, respectively. The results are shown in the lower panel in FIG. 2 (d). As illustrated in the lower panel in FIG. 2 (d), each of WT-FLAG and ΔCRD-2-FLAG formed a complex with CKAP4 but ΔCRD-1-FLAG did not form a complex with CKAP4. In agreement with the above-mentioned reports, each of WT-FLAG and ΔCRD-2-FLAG formed a complex with LRP6 but ΔCRD-2-FLAG did not form a complex with LRP6. Consequently, it was found that Dkk1 formed a complex with each of CKAP4 and LRP6 through a different domain.

In the upper panel in FIG. 2 (e), the schematic illustrations of domain structures of CKAP4 which were used in this test are shown. In the upper panel in FIG. 2 (e), ICD represents an intracellular domain, ECD represents an extracellular domain, E represents an endoplasmic reticulum anchor domain, MB represents a microtubule-binding domain, M represents a transmembrane domain, T represents a tyrosine-sulfated domain, LZ represents a leucine zipper domain, and a represents an α-helix domain.

A lysate (Input) of X293T/Dkk1-FLAG cells in which wild-type CKAP4-HA(WT) or a deletion mutant CKAP4-HA (ECD, ΔC1, ΔC2, ΔC3) was transiently expressed was immunoprecipitated with an anti-FLAG antibody. Subsequently, each of the cell lysate (Input) and the immunoprecipitates (IP) was probed with an anti-HA antibody or an anti-Dkk1 antibody. The results are shown in the lower left panels in FIG. 2 (e). From the results, it was found that Dkk1 formed a complex with ΔC1 but did not form a complex with ΔC2 or ΔC3 in an extracellular domain of CKAP4. Namely, a possibility that the N-terminal side of Dkk1 was bound to a leucine zipper domain of CKAP4 was suggested.

A lysate (Input) of X293T/Dkk1-FLAG cells in which wild-type CKAP4-HA (WT) or a deletion mutant CKAP4-HA (ΔLZ) was transiently expressed was immunoprecipitated with an anti-FLAG antibody, and then the cell lysate (Input) and the immunoprecipitates (IP) were subjected to the detection of HA and Dkk1 using an anti-HA antibody and an anti-Dkk1 antibody, respectively. The results are shown in the lower right panel in FIG. 2 (e). From the results, it was found that Dkk1 did not form a complex with ΔLZ. Namely, it was confirmed that a CRD-1 domain located on the N-terminal side of Dkk1 and a leucine zipper domain of CKAP4 were necessary for the binding between Dkk1 and CKAP4.

Figure 3:
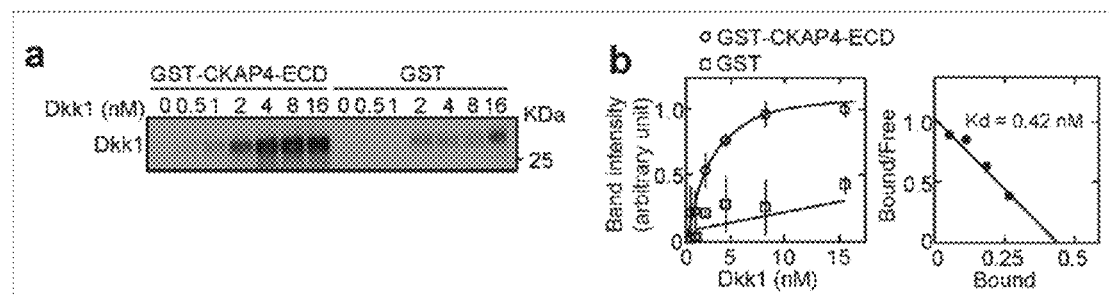
FIGS. 3 (a) and (b) show the results obtained by incubating a polypeptide (GST-CKAP4-ECD), in which glutathione-S-transferase (GST) was linked to the N-terminal of an extracellular domain (ECD) of CKAP4, or GST together with Dkk1 and then detecting and measuring Dkk1 bound to GST-CKAP4-ECD or GST.

A polypeptide (GST-CKAP4-ECD) (a mutant in which an intracellular domain was deleted) was provided, in which glutathione-S-transferase (GST) was linked to the N-terminal of an extracellular domain (ECD) of CKAP4 (which is located between position-128 to position-602 in the amino acid sequence represented by SEQ ID NO: 1). In 500 μl of NP40 buffer, 0.5 nM of GST-CKAP4-ECD or 0.5 nM of GST was reacted with 0 to 16 nM of Dkk1 (R&D Systems) for 2 hours at 4° C. Subsequently, GST-CKAP4-ECD and GST were collected by centrifugation and then washed with NP40 buffer three times. The resultant precipitates were subjected to the detection of Dkk1 using an anti-Dkk1 antibody. The results are shown in FIGS. 3 (a) and (b). From the results, it was confirmed that Dkk1 was bound to an extracellular domain of CKAP4 directly.

Figure 4:
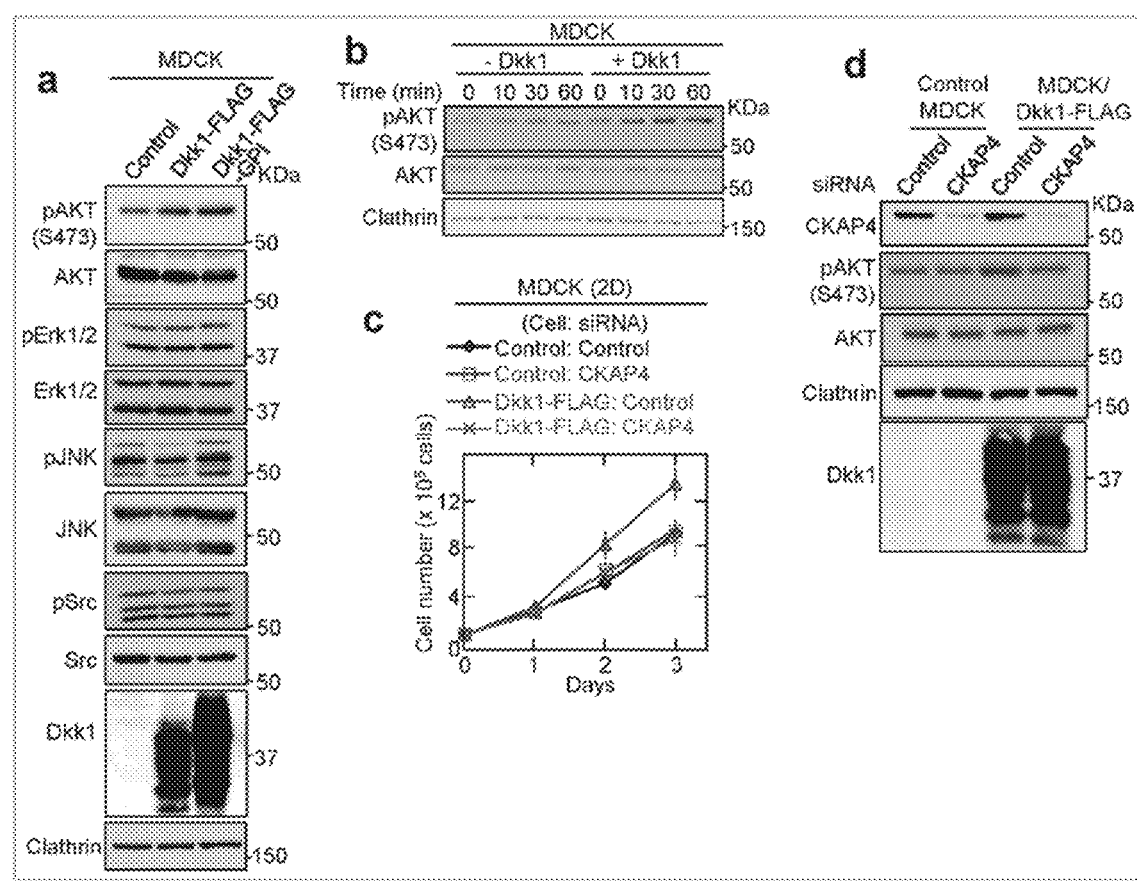
FIG. 4 (a) shows the results of the detection of the states of phosphorylation of various proteins in a lysate of MDCK cells (control), MDCK/Dkk1-FLAG cells (Dkk1-FLAG) or MDCK/Dkk1-FLAG-GPI cells (Dkk1-FLAG-GPI).

2-3. Confirmation of Influence of Dkk1 on Phosphorylation of AKT and Enhancement of Proliferation in MDCK Cells A lysate of MDCK cells (WT), MDCK/Dkk1-FLAG cells (Dkk1-FLAG) or MDCK/Dkk1-GPI1-FLAG cells (Dkk1-FLAG-GPI) was reacted with an antibody against each of various proteins shown in FIG. 4 (a). As a result, as shown in FIG. 4 (a), the phosphorylation of AKT was enhanced but the enhancement of the phosphorylation of ErK1/2, MK and Src was not observed in MDCK cells when Dkk1 was overexpressed. Namely, it was suggested that Dkk1 activated AKT.

MDCK cells was treated with 1 nM of nocodazole for 24 hours, and then the MDCK cells were stimulated with a preparation solution containing 250 ng/ml of Dkk1 or a Dkk1-free preparation solution for 60 minutes. The cells were collected 0, 10, 30 and 60 minutes after the initiation of the stimulation to prepare cell lysates. Subsequently, the cell lysates were subjected to the detection of pAKT, AKT and clathrin using an anti-pAKT antibody, an anti-AKT antibody and an anti-clathrin antibody, respectively. Clathrin was used as a loading control. The results are shown in FIG. 4 (b). From the results, it was demonstrated that the phosphorylation of AKT in MDCK cells was enhanced in the presence of Dkk1, and it was suggested that Dkk1 activated AKT in a time-dependent manner.

MDCK cells (control) or MDCK/Dkk1-FLAG cells (Dkk1-FLAG) were transfected with control siRNA or CKAP4 siRNA. The resultant cells were subjected to a cell proliferation assay. The results are shown in FIG. 4 (c). From the results, it was confirmed that the decrease in cell proliferation ability was observed when the expression of CKAP4 was suppressed in the Dkk1-expressing cells and therefore Dkk1 enhanced the proliferation of cells through CKAP4.

MDCK cells (control) or MDCK/Dkk1-FLAG cells were transfected with control siRNA or CKAP4 siRNA. A lysate of the resultant cells was prepared, and then the lysate was reacted with an antibody against each of various proteins shown in FIG. 4 (d), thereby detecting the various proteins. The results are shown in FIG. 4 (d). As a result, it was found that, when Dkk1 was expressed, the phosphorylation of AKT was significantly decreased by suppressing the expression of CKAP4. Therefore, it was suggested that Dkk1 and CKAP4 were needed for the activation of AKT in MDCK cells.

Figure 5:
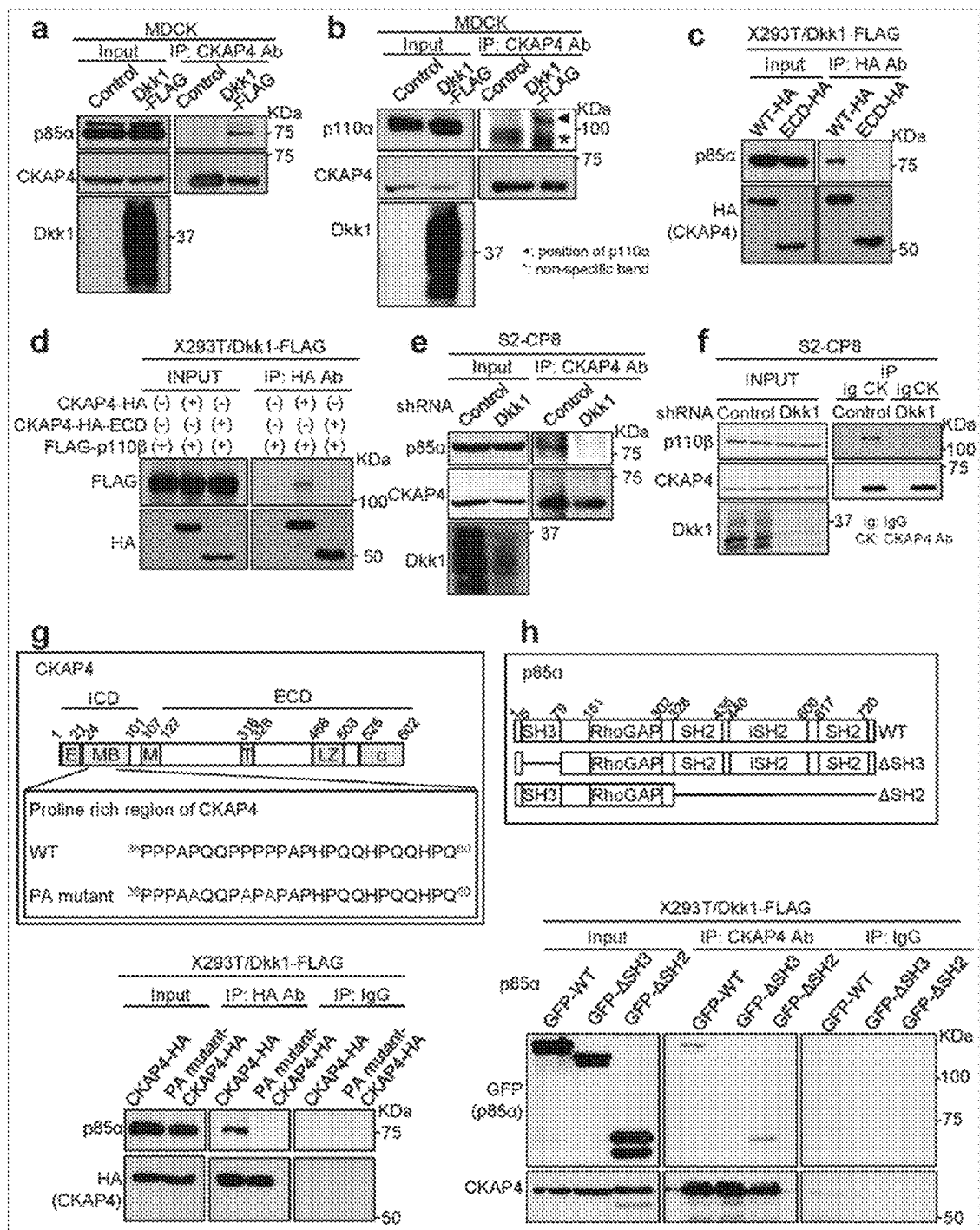
FIG. 5 (a) shows the results of the detection of p85α, CKAP4 and Dkk1 in the immunoprecipitates (IP) of a lysate (Input) of each of a control (MDCK cells) and MDCK cells (MDCK/Dkk1-FLAG) overexpressing wild-type Dkk1-FLAG (WT) with an anti-CKAP4 antibody.

In order to clarify the mechanism of activation of AKT by CKAP4, a lysate (Input) of each of a control (MDCK cells) and MDCK cells (MDCK/Dkk1-FLAG) overexpressing wild-type Dkk1-FLAG(WT) was immunoprecipitated with an anti-CKAP4 antibody. Subsequently, the cell lysate (Input) and the immunoprecipitates (IP) were subjected to the detection of p85α, p110α, CKAP4 and Dkk1 using an anti-p85α antibody, an anti-p110α antibody, an anti-CKAP4 antibody and an anti-Dkk1 antibody, respectively. The results are shown in FIGS. 5 (a) and (b). From the results, it was found that CKAP4 was bound to p85α and p110α, which constitute PI3K, in cells in which Dkk1 was overexpressed. Namely, from the results, it was suggested that CKAP4 was bound to PI3K to activate AKT in cells in which Dkk1 was overexpressed.

In X293T/Dkk1-FLAG cells, CKAP4-HA or CKAP4-ECD-HA was caused to be expressed together with p85a. A lysate (Input) of the resultant cells was prepared. The lysate was immunoprecipitated with an anti-HA antibody. Subsequently, the cell lysate (Input) and the immunoprecipitates (IP) were subjected to the detection of p85α and CKAP4 using an anti-p85α antibody and an anti-HA antibody, respectively. The results are shown in FIG. 5 (c). From the results, it was found that an intracellular domain of CKAP4 was needed for the Dkk1-dependent binding between CKAP4 and p85a.

In X293T/Dkk1-FLAG cells, CKAP4-HA or CKAP4-HA ECD was caused to be expressed together with FLAG-p110β. A lysate (Input) of the resultant cells was prepared. The lysate was immunoprecipitated with an anti-HA antibody. Subsequently, the cell lysate (Input) and the immunoprecipitates (IP) were subjected to the detection of p110β and CKAP4 using an anti-p110β antibody or an anti-HA antibody, respectively. The results are shown in FIG. 5 (d). From the results, it was found that an intracellular domain of CKAP4 was needed for the Dkk1-dependent binding between CKAP4 and p110β.

A lysate (Input) of S2-CP8 cells in which control shRNA or Dkk1 shRNA (Dkk1) was stably expressed was prepared. The lysate was immunoprecipitated with an anti-CKAP4 antibody. Subsequently, the cell lysate (Input) and the immunoprecipitates (IP) were subjected to the detection of p85α, p110β, CKAP4 and Dkk1 using an anti-p85α antibody, an anti-p110β antibody, an anti-CKAP4 antibody and an anti-Dkk1 antibody, respectively. The results are shown in FIGS. 5 (e) and (f). From the results, it was found that CKAP4 also formed a complex with each of p85α and p110β in a Dkk1-dependent manner in S2-CP8 cells.

In the upper panel in FIG. 5 (g), the amino acid sequence for a proline-rich domain of CKAP4 is shown. As shown in the upper panel in FIG. 5 (g), a gene encoding a CKAP4 mutant (PA mutant-CKAP4-HA), in which some of proline residues were respectively substituted by alanine residues in the proline-rich domain of CKAP4, was produced. A lysate of X293T/Dkk1-FLAG cell transfected with a gene encoding CKAP4-HA or PA mutant-CKAP4-HA was immunoprecipitated with an anti-HA antibody or a non-immune antibody. The cell lysate (Input) and the immunoprecipitates (IP) were subjected to the detection of p85α and HA using an anti-p85α antibody and an anti-HA antibody, respectively. The results are shown in the lower panel in FIG. 5 (g). From the results, it was confirmed that, when a proline residue in the proline-rich domain of CKAP4 was substituted by an alanine residue, the binding between CKAP4 and PI3K was inhibited.

In the upper panel in FIG. 5 (h), the schematic illustration of the domain structure of p85α is shown. As shown in the upper panel in FIG. 5 (h), genes respectively encoding wild-type p85α (WT) (GFP-WT), ΔSH3 in which SH3 domain was deleted (GFP-ΔSH3) and ΔSH2 in which SH2 and iSH2 domains were deleted (GFP-ΔSH2) were produced. A lysate of X293T/Dkk1-FLAG cells transfected with a gene encoding GFP-WT, GFP-ΔSH3 or GFP-ΔSH2 was immunoprecipitated with an anti-CKAP4 antibody or a non-immune antibody. The cell lysate (Input) and the immunoprecipitates (IP) were subjected to the detection of GFP (p85α) and CKAP4 using an anti-GFP(p85α) antibody and an anti-CKAP4 antibody, respectively. The results are shown in the lower panel in FIG. 5 (h). From the results, it was found that a SH3 domain of p85α (PI3K) involved in the binding to CKAP4.

2-4. Confirmation of Expression of Dkk1 and CKAP4 in Cultured Cell Strains

Figure 6:
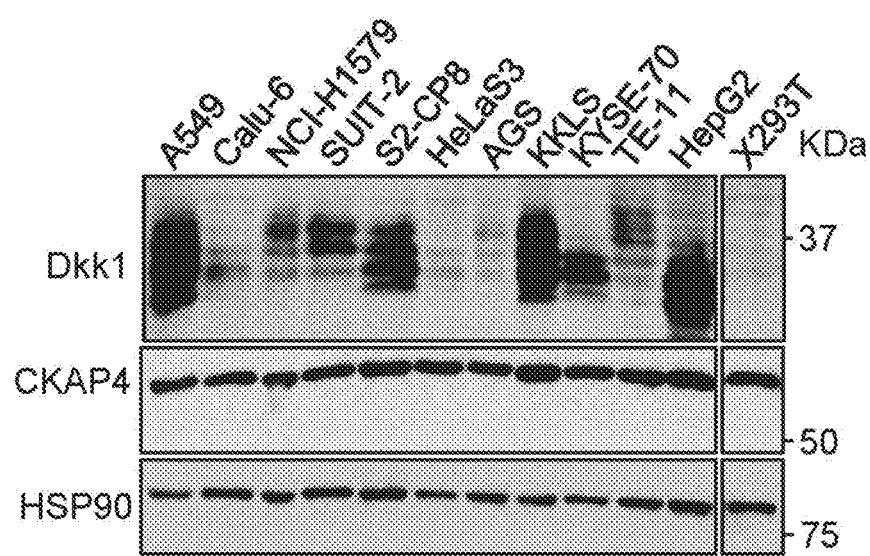
FIG. 6 shows the results of the detection of Dkk1, CKAP4 and HSP90 in each of lysates of lung cancer cells, pancreatic cancer cells, cervical canal cancer cells, gastric cancer cells, esophageal squamous cell carcinoma cells, liver cancer cells and fetal kidney cells.

A lysate of each of lung cancer cells (A549, Calu-6 and NCI-H1579), pancreatic cancer cells (SUIT-2 and S2-CP8), cervical canal cancer cells (HeLaS3), gastric cancer cells (AGS and KKLS), esophageal squamous cell carcinoma cells (KYSE-70 and TE-11), hepatoblastoma cells (HepG2) and fetal kidney cells (X239T) was reacted with each of an anti-Dkk1 antibody, an anti-CKAP4 antibody and an anti-HSP90 antibody, and the amounts of Dkk1, CKAP4 and HSP90 (control) were measured. The results are shown in FIG. 6. From the results, it was confirmed that Dkk1 was not expressed in normal cells and was expressed in some of cancer cells while CKAP4 was expressed in all of the cells.

Figure 7:
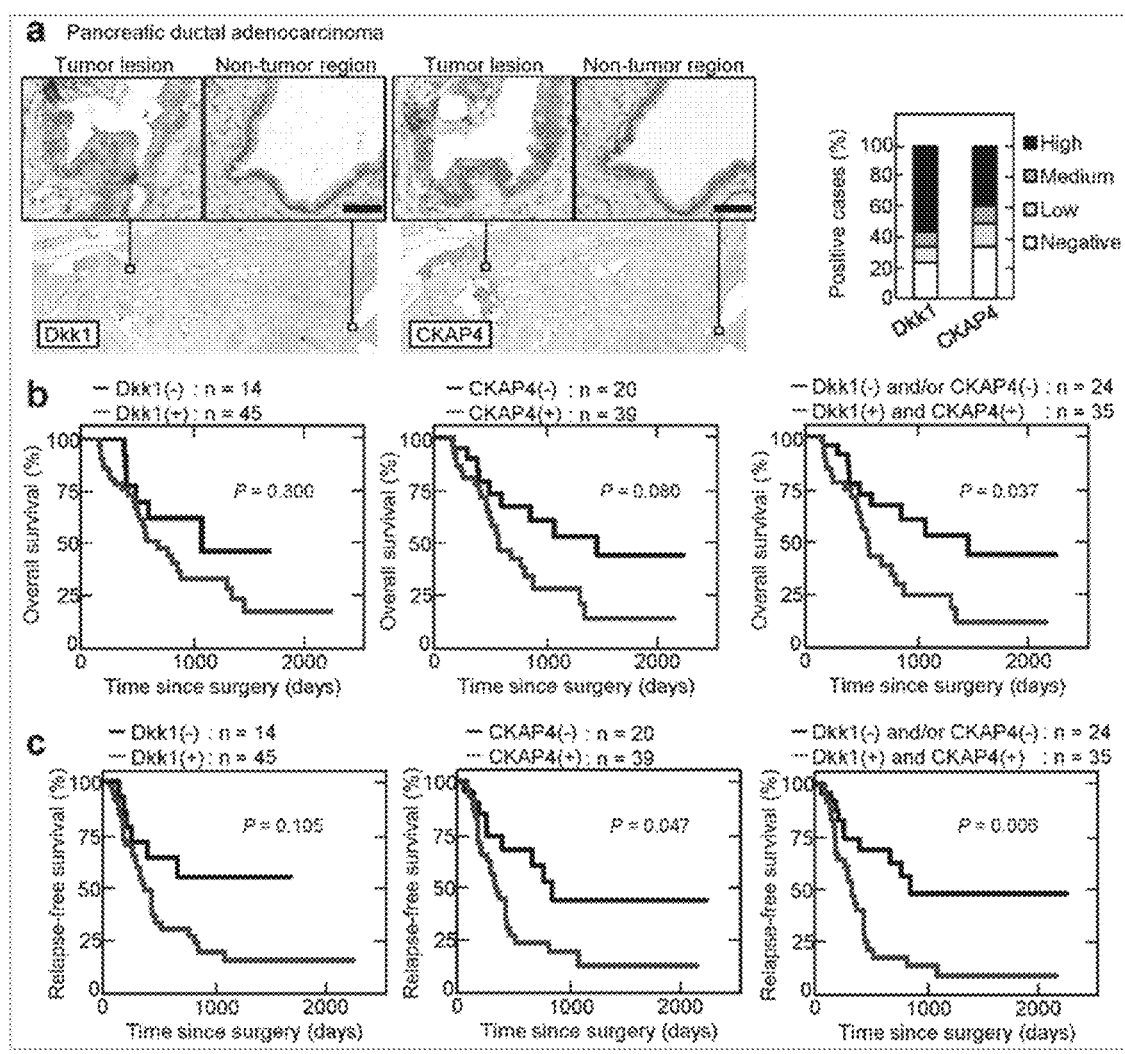
FIG. 7 (a) shows the results of the immunostaining of a pancreatic cancer tissue extirpated from a pancreatic cancer patient with an anti-Dkk1 antibody or an anti-CKAP4 antibody and haematoxylin (in the left panel) and the results of the classification of pancreatic cancer tissues (n=59) extirpated from pancreatic cancer patients on the basis of the expression amounts of Dkk1 and CKAP4 (in the right panel).

2-5. Confirmation of Correlation Between Tumor-Tissue-Specific Expression of Dkk1 and CKAP4 in Pancreatic Cancer, Lung Adenocarcinoma, and Lung Squamous Cell Carcinoma and Prognosis The results of the immunostaining of pancreatic cancer tissues respectively extirpated from pancreatic cancer patients tissue (n=59) with an anti-Dkk1 antibody or an anti-CKAP4 antibody and haematoxylin are shown in the left panels in FIG. 7 (a). In the upper left panel in FIG. 7 (a), the boxed areas are enlarged images of tumor regions. In the upper right panel in FIG. 7 (a), the boxed areas are enlarged images of non-tumor tumor regions. In the left panels in FIG. 7 (a), the scale bar indicates 50 μm. In the right panel in FIG. 7 (a), "low" represents a case in which a region in which Dkk1 or CKAP4 was expressed made up 5% or more and less than 20% of a tumor region, "medium" represents a case in which a region in which Dkk1 or CKAP4 was expressed made up 20% or more and less than 50% of a tumor region, and "high" represents a case in which a region in which Dkk1 or CKAP4 was expressed made up 50% or more of a tumor region. A case in which the expression was observed in 5% or less of a tumor region was determined as "negative". From the results, it was confirmed that Dkk1 and CKAP4 were expressed at frequency of as high as 76.3% and 66.1%, respectively, in pancreatic cancer cases. In FIGS. 7 (b) and (c), the results obtained by classifying each type of samples on the basis of the presence or absence of the expression of Dkk1 and CKAP4 and analyzing the relationship between days after operation and an overall survival rate and a relapse-free survival rate are shown. From these results, it was found that, in a pancreatic cancer patient in whom both of Dkk1 and CKAP4 were expressed, the shortening of a post-operative overall survival period and a relapse-free survival period was observed.

Figure 8:
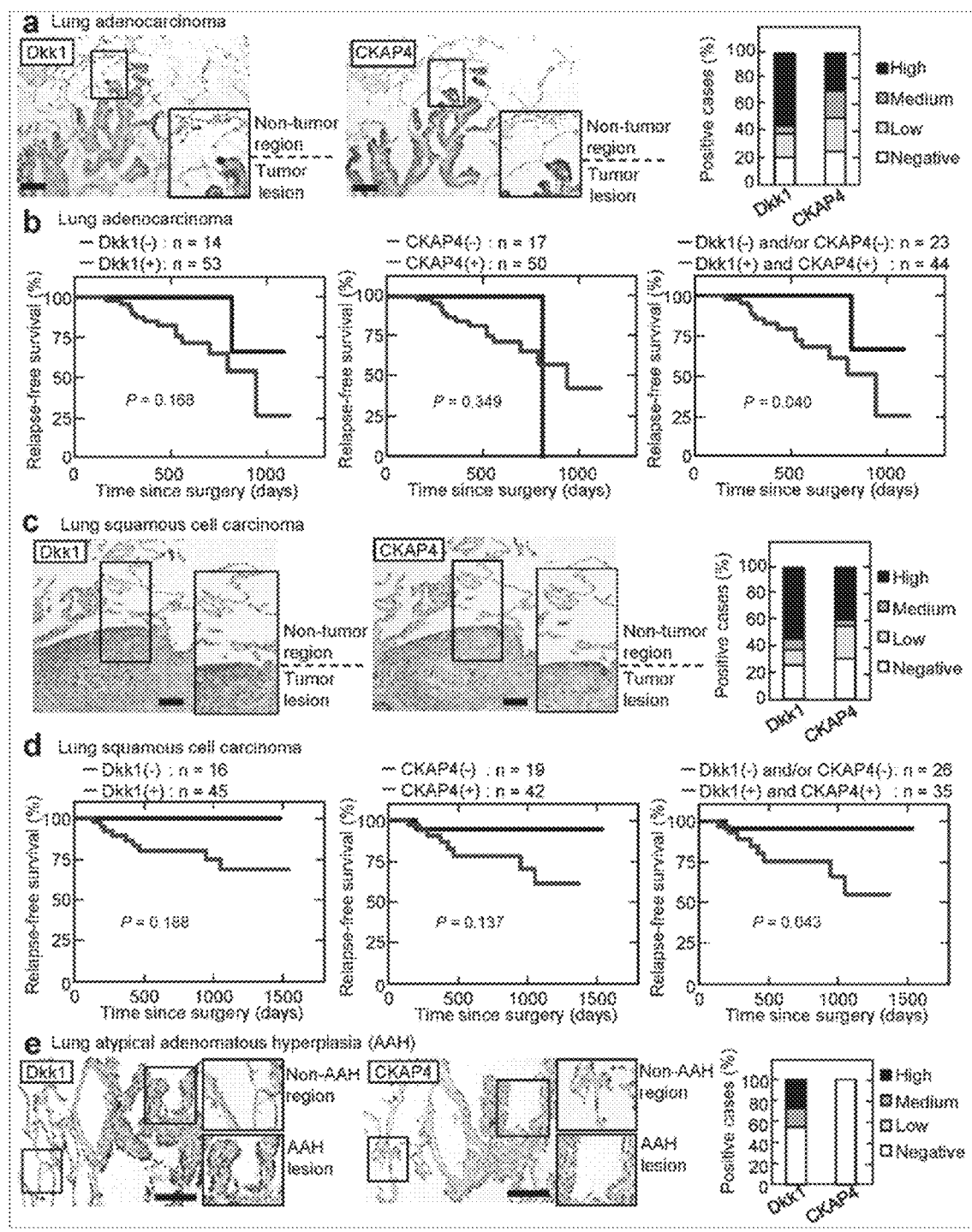
FIG. 8 (a) shows the results of the immunostaining of lung adenocarcinoma tissues extirpated from lung adenocarcinoma patients with an anti-Dkk1 antibody or an anti-CKAP4 antibody and haematoxylin (in the left panels) and the results of the classification of lung adenocarcinoma tissues extirpated from lung adenocarcinoma patients (n=67) on the basis of the expression amounts of Dkk1 and CKAP4 (in the right panel).

The results of the immunostaining of lung adenocarcinoma tissues (n=67) with an anti-Dkk1 antibody or an anti-CKAP4 antibody and haematoxylin are shown in the left panels in FIG. 8 (a). In the left panels in FIG. 8 (a), each of boxed areas is an enlarged image of a tumor region or a non-tumor region. In the left panels in FIG. 8 (a), the scale bar indicates 100 μm. In the right panel in FIG. 8 (a), "low" represents a case in which a region in which Dkk1 or CKAP4 was expressed made up 5% or more and less than 20% of a tumor region, "medium" represents a case in which a region in which Dkk1 or CKAP4 was expressed made up 20% or more and less than 50% of a tumor region, and "high" represents a case in which a region in which Dkk1 or CKAP4 was expressed made up 50% or more of a tumor region. A case in which a region in which Dkk1 or CKAP4 was expressed made up 5% or less was determined as "negative". From the results, it was confirmed that Dkk1 and CKAP4 were expressed at frequencies as high as 79.1% and 74.6%, respectively, in lung adenocarcinoma cases. In FIG. 8 (b), the results obtained by classifying each type of samples on the basis of the presence or absence of the expression of Dkk1 and CKAP4 and analyzing the relationship between days after operation and a relapse-free survival rate are shown. From these results, the shortening of the relapse-free survival period was observed in lung adenocarcinoma patients in whom both of Dkk1 and CKAP4 were expressed.

The results of the immunostaining of lung squamous cell carcinoma tissues (n=61) extirpated from lung squamous cell carcinoma patients with an anti-Dkk1 antibody or an anti-CKAP4 antibody and haematoxylin are shown in the left panels in FIG. 8 (c). In the left panels in FIG. 8 (c), each of boxed areas is an enlarged image of a tumor region or a non-tumor region. In the left panels in FIG. 8 (c), the scale bar indicates 100 μm. In the right panel in FIG. 8 (c), "low" represents a case in which a region in which Dkk1 or CKAP4 was expressed made up 5% or more and less than 20% of a tumor region, "medium" represents a case in which a region in which Dkk1 or CKAP4 was expressed made up 20% or more and less than 50% of a tumor region, and "high" represents a case in which a region in which Dkk1 or CKAP4 was expressed made up 50% or more of a tumor region. A case in which a region in which Dkk1 or CKAP4 was expressed made up 5% or less was determined as "negative". From the results, it was confirmed that Dkk1 and CKAP4 were expressed at frequencies as high as 73.8% and 68.9%, respectively, in lung squamous cell carcinoma cases. In FIG. 8 (d), the results obtained by classifying each type of samples on the basis of the presence or absence of the expression of Dkk1 and CKAP4 and analyzing the relationship between days after operation and a relapse-free survival rate are shown. From these results, it was found that the shortening of the relapse-free survival period was observed in lung squamous cell carcinoma patients in whom both of Dkk1 and CKAP4 were expressed.

The results of the immunostaining of lung tissues (n=11) having lung atypical adenomatous hyperplasia (AAH) with an anti-Dkk1 antibody or an anti-CKAP4 antibody and haematoxylin are shown in the left panels in FIG. 8 (e). In the left panels in FIG. 8 (e), each of boxed areas is an enlarged image of a tumor region or a non-tumor region. In the left panels in FIG. 8 (e), the scale bar indicates 100 μm. In the right panel in FIG. 8 (e), "low" represents a case in which a region in which Dkk1 or CKAP4 was expressed made up 5% or more and less than 20% of an AAH region, "medium" represents a case in which a region in which Dkk1 or CKAP4 was expressed made up 20% or more and less than 50% of an AAH region, and "high" represents a case in which a region in which Dkk1 or CKAP4 was expressed made up 50% or more of an AAH region. A case in which a region in which Dkk1 or CKAP4 was expressed made up 5% or less was determined as "negative". From the results, in light of the fact that the expression of CKAP4 was negative even though the expression of Dkk1 was positive in AAH and AAH was a precancerous lesion, a possibility that the expression of CKAP4 was involved in the transition of a precancerous lesion of lung cancer into cancer was suggested.

Figure 9:
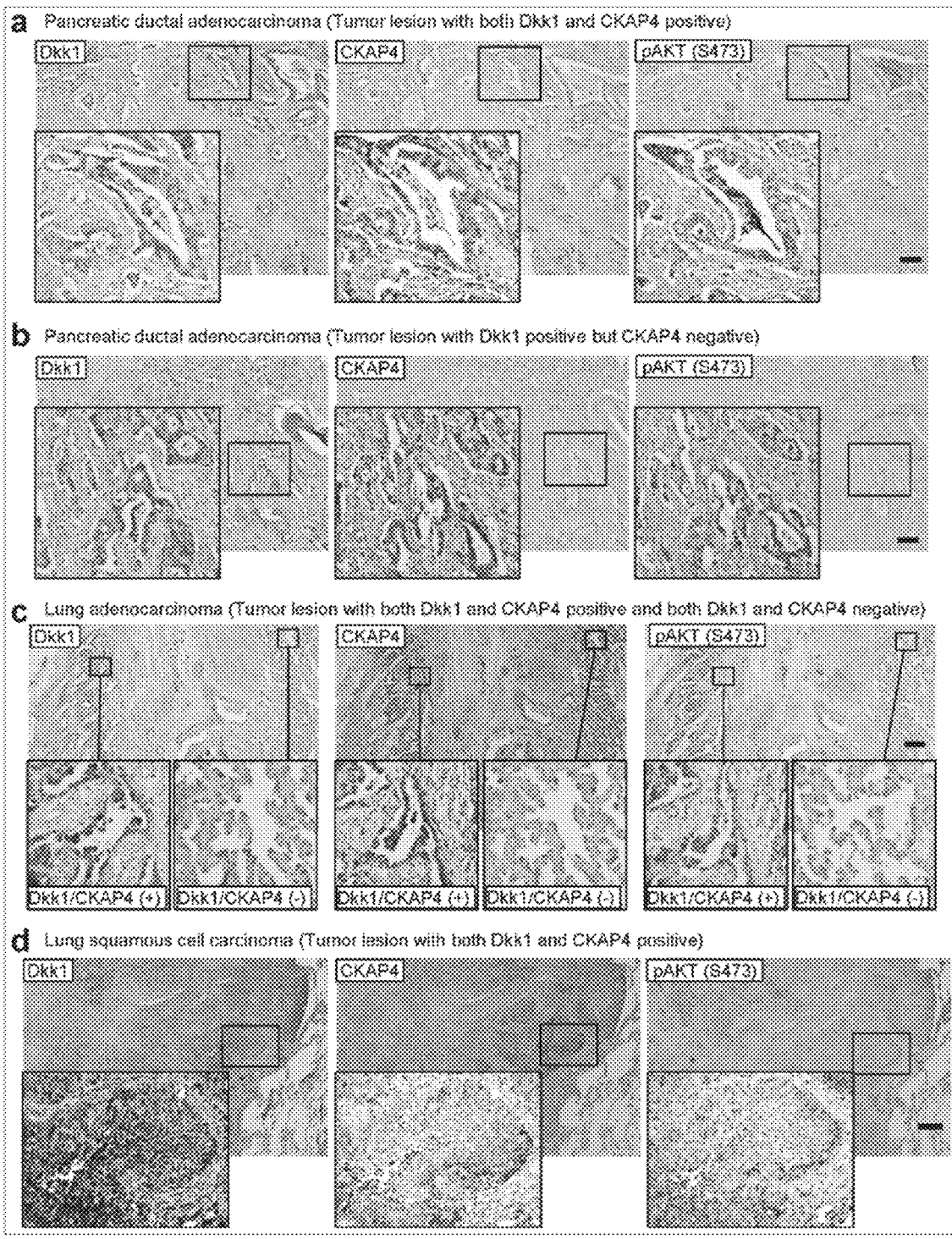
FIG. 9 shows the results of the immunostaining of cancer tissues of human pancreatic cancer (a, b), human lung adenocarcinoma (c) and human lung squamous cell carcinoma (d) with an anti-Dkk1 antibody, an anti-CKAP4 antibody or an anti-pAKT antibody and haematoxylin.

2-6. Confirmation of Expression of Dkk1 and CKAP4 and Activation of AKT in Human Pancreatic Cancer, Human Lung Adenocarcinoma and Human Lung Squamous Cell Carcinoma Cancer tissues of each of human pancreatic cancer, human lung adenocarcinoma and human lung squamous cell carcinoma were immunostained with an anti-Dkk1 antibody, an anti-CKAP4 antibody or an anti-pAKT antibody and haematoxylin. The results are shown in FIG. 9. In FIG. 9, each of black boxes is an enlarged image, and the bar scale indicates 200 μm. From the results, it was confirmed that, in human pancreatic cancer, human lung adenocarcinoma and human lung squamous cell carcinoma examined in the test, AKT was activated in a tumor region in which Dkk1 and CKAP4 were expressed.

2-7. Confirmation of Influence of Dkk1-CKAP4 Signal on Proliferation of Tumor Cells S2-CP8 cells were transfected with control shRNA, Dkk1 shRNA, Dkk1 shRNA and Dkk1-FLAG, CKAP4 shRNA, or CKAP4shRNA and CKAP4-HA. A lysate of the resultant cells was prepared, and the lysate was subjected to the detection of various proteins shown in the upper panels in FIG. 10 (a) using antibodies against the proteins, respectively. The cells were also subjected to a cell proliferation assay. The results are shown in the lower panel in FIG. 10 (a). From the results, it was confirmed that the activity of AKT was inhibited to decrease a cell proliferation ability when the expression of Dkk1 or CKAP4 was suppressed in S2-CP8 cells and the activity of AKT and the proliferation of cells were able to recover by causing the overexpression of Dkk1 or CKAP4 in the cells.

A549 cells were transfected with control shRNA, Dkk1 shRNA, Dkk1 shRNA and Dkk1-FLAG, CKAP4 shRNA, or CKAP4 shRNA and CKAP4-HA. A lysate of the resultant cells was prepared, and the lysate was subjected to the detection of various proteins shown in the upper panels in FIG. 10 (b) using antibodies against the proteins, respectively. The cells were also subjected to a cell proliferation assay. The results are shown in the lower panel in FIG. 10 (b). From the results, it was confirmed that the activity of AKT was inhibited to decrease a cell proliferation ability when the expression of Dkk1 or CKAP4 was suppressed in A549 cells and the activity of AKT and the proliferation of cells were able to recover by causing the overexpression of Dkk1 or CKAP4 in the A549 cells.

Figure 10:
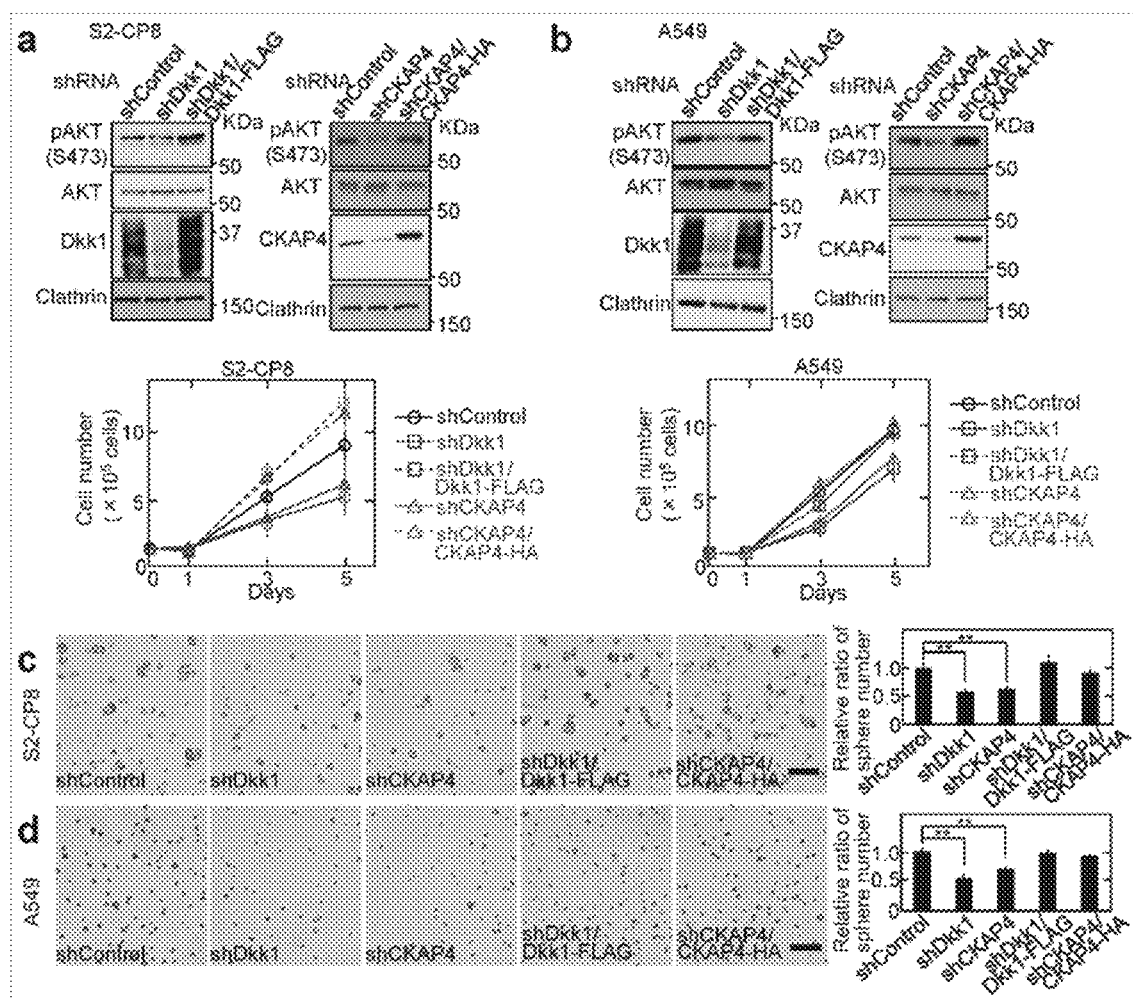
FIG. 10 (a) shows the results of the detection of various proteins in a lysate of S2-CP8 cells transfected with control shRNA, Dkk1 shRNA, or Dkk1 shRNA and Dkk1-FLAG (in the upper left panel), the results of the detection of various proteins in a lysate of S2-CP8 cells transfected with control shRNA, CKAP4 shRNA, or CKAP4 shRNA and CKAP4-HA (in the upper right panel), and the results of a cell proliferation assay on each of the cells (in the lower panel).

S2-CP8 cells ($2\times10^4$ cells) or A549 cells ($2\times10^4$ cells) expressing control shRNA, Dkk1 shRNA, Dkk1 shRNA and Dkk1-FLAG, or CKAP4 shRNA or CKAP4 shRNA and CKAP4-HA were cultured three-dimensionally on a matrigel for 5 days. The number of spheroids per 1 mm$^2$ was counted (in five fields). The results are shown in FIGS. 10 (c) and (d). From the results, it was confirmed that the number of spheroids in S2-CP8 cells and A549 cells in which the expression of Dkk1 or CKAP4 was suppressed decreased compared with that in the control and the formation of tumor was able to be suppressed by suppressing the expression of Dkk1 or CKAP4 and was able to recover by causing the overexpression of Dkk1 or CKAP4.

Figure 11:
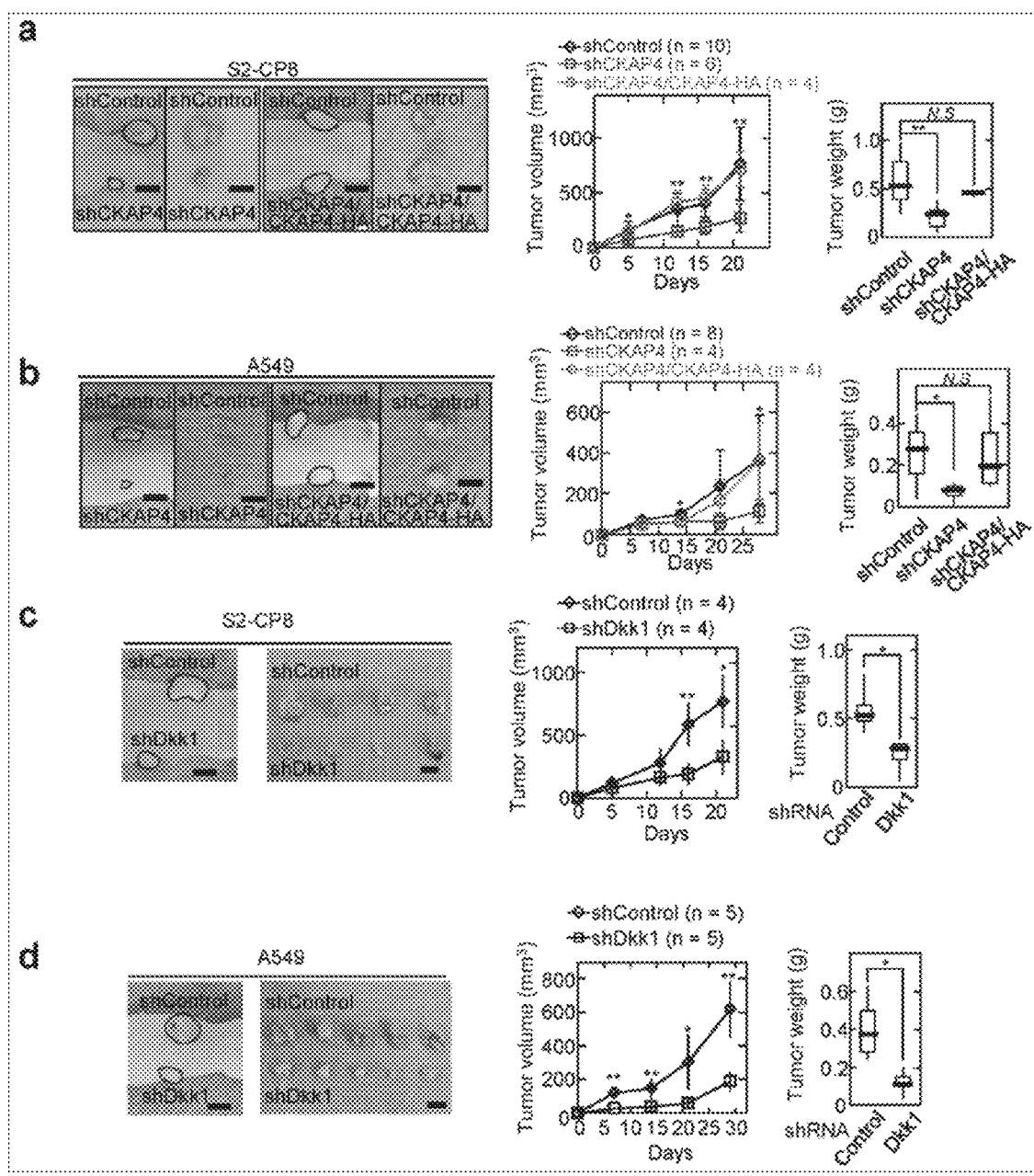
FIG. 11 (a) shows the results of the analysis on the change in tumor volume of a tumor xenograft during the period of 21 days after injection and the final weight of the tumor xenograft in nude mice which received the subcutaneous injection of S2-CP8 cells expressing control shRNA, CKAP4 shRNA, or CKAP4 shRNA and CKAP4-HA.

S2-CP8 cells ($5 \times 10^6$ cells) expressing control shRNA, CKAP4 shRNA, or CKAP4 shRNA and CKAP4-HA were injected subcutaneously to the back of each of nude mice. After 21 days, a tumor xenograft in a transplanted site in each of the nude mice was analyzed. The results are shown in FIG. 11 (a). In the left panel in FIG. 11 (a), the results of the observation of the nude mice from above after 21 days and the results of the observation of the extirpated tumor xenografts are shown. In FIG. 11 (a), the broken lines represent the outline forms of the tumor xenografts, and each of the scale bars indicates 10 mm. In the middle panel in FIG. 11 (a), the results of the measurement of the sizes of the tumor tissue sections are shown. In the right panel in FIG. 11 (a), the results of the measurement of the weights of the tumor xenografts are shown. In the right panel in FIG. 11 (a), the median is represented with a bold line, the box represents the $25^{th}$-$75^{th}$ percentile range, the error bars represent the $5^{th}$-$95^{th}$ percentile ranges, * represents $P<0.05$; and ** represents $P<0.01$. From the results, it was confirmed that the tumor formation ability of S2-CP8 cells decreased by suppressing the expression of CKAP4 and recovered by causing the overexpression of CKAP4.

A549 cells ($5 \times 10^6$ cells) expressing control shRNA, CKAP4 shRNA, or CKAP4 shRNA and CKAP4-HA were injected subcutaneously to the back of each of nude mice. After 28 days, a tumor xenograft in a transplanted site in each of the nude mice was analyzed. The results are shown in FIG. 11 (b). In the left panel in FIG. 11 (b), the results of the observation of the nude mice from above after 28 days and the results of the observation of the extirpated tumor xenografts are shown. In FIG. 11 (b), the broken lines represent the outline forms of the tumor xenografts, and each of the scale bars indicates 10 mm. In the middle panel in FIG. 11 (b), the results of the measurement of the sizes of the tumor tissue sections are shown. In the right panel in FIG. 11 (b), the results of the measurement of the weights of the tumor xenografts are shown. In the right panel in FIG. 11 (b), the median is represented with a bold line, the box represents the $25^{th}$-$75^{th}$ percentile range, the error bars represent the $5^{th}$-$95^{th}$ percentile ranges, * represents $P<0.05$; and ** represents $P<0.01$. From the results, it was confirmed that the tumor formation ability of A549 cells decreased by suppressing the expression of CKAP4 and recovered by causing the overexpression of CKAP4.

S2-CP8 cells ($5 \times 10^6$ cells) expressing control shRNA or Dkk1 shRNA were injected subcutaneously to the back of each of nude mice. After 21 days, a tumor xenograft in a transplanted site in each of the nude mice was analyzed. The results are shown in FIG. 11 (c). In the left panel in FIG. 11 (c), the results of the observation of the nude mice from above after 21 days and the results of the observation of the extirpated tumor xenografts are shown. In FIG. 11 (c), the broken lines represent the outline forms of the tumor xenografts, and each of the scale bars indicates 10 mm. In the middle panel in FIG. 11 (c), the results of the measurement of the sizes of the tumor tissue sections are shown. In the right panel in FIG. 11 (c), the results of the measurement of the weights of the tumor xenografts are shown. In the right panel in FIG. 11 (a), the median is represented with a bold line, the box represents the $25^{th}$-$75^{th}$ percentile range, the error bars represent the $5^{th}$-$95^{th}$ percentile ranges, represents $P<0.05$; and ** represents $P<0.01$. From the results, it was confirmed that the tumor formation ability of S2-CP8 cells decreased by suppressing the expression of Dkk1.

A549 cells ($5 \times 10^6$ cells) expressing control shRNA or Dkk1 shRNA were injected subcutaneously to the back of each of nude mice. After 28 days, a tumor xenograft in a transplanted site in each of the nude mice was analyzed. The results are shown in FIG. 11 (d). In the left panel in FIG. 11 (d), the results of the observation of the nude mice from above after 28 days and the results of the observation of the extirpated tumor xenografts are shown. In FIG. 11 (d), the broken lines represent the outline forms of the tumor xenografts, and each of the scale bars indicates 10 mm. In the middle panel in FIG. 11 (d), the results of the measurement of the sizes of the tumor tissue sections are shown. In the right panel in FIG. 11 (d), the results of the measurement of the weights of the tumor xenografts are shown. In the right panel in FIG. 11 (d), the median is represented with a bold line, the box represents the $25^{th}$-$75^{th}$ percentile range, the error bars represent the $5^{th}$-$95^{th}$ percentile ranges, * represents $P<0.05$; and ** represents $P<0.01$. From the results, it was confirmed that the tumor formation ability of A549 cells decreased by suppressing the expression of Dkk1.

2-8. Confirmation of Effect of Anti-CKAP4 Antibody to Inhibit Binding Between Dkk1 and CKAP4, and Confirmation of Effect of Anti-CKAP4 Antibody to Suppress Proliferation in Cancer Cells Expressing Dkk1 and CKAP4

Figure 12:
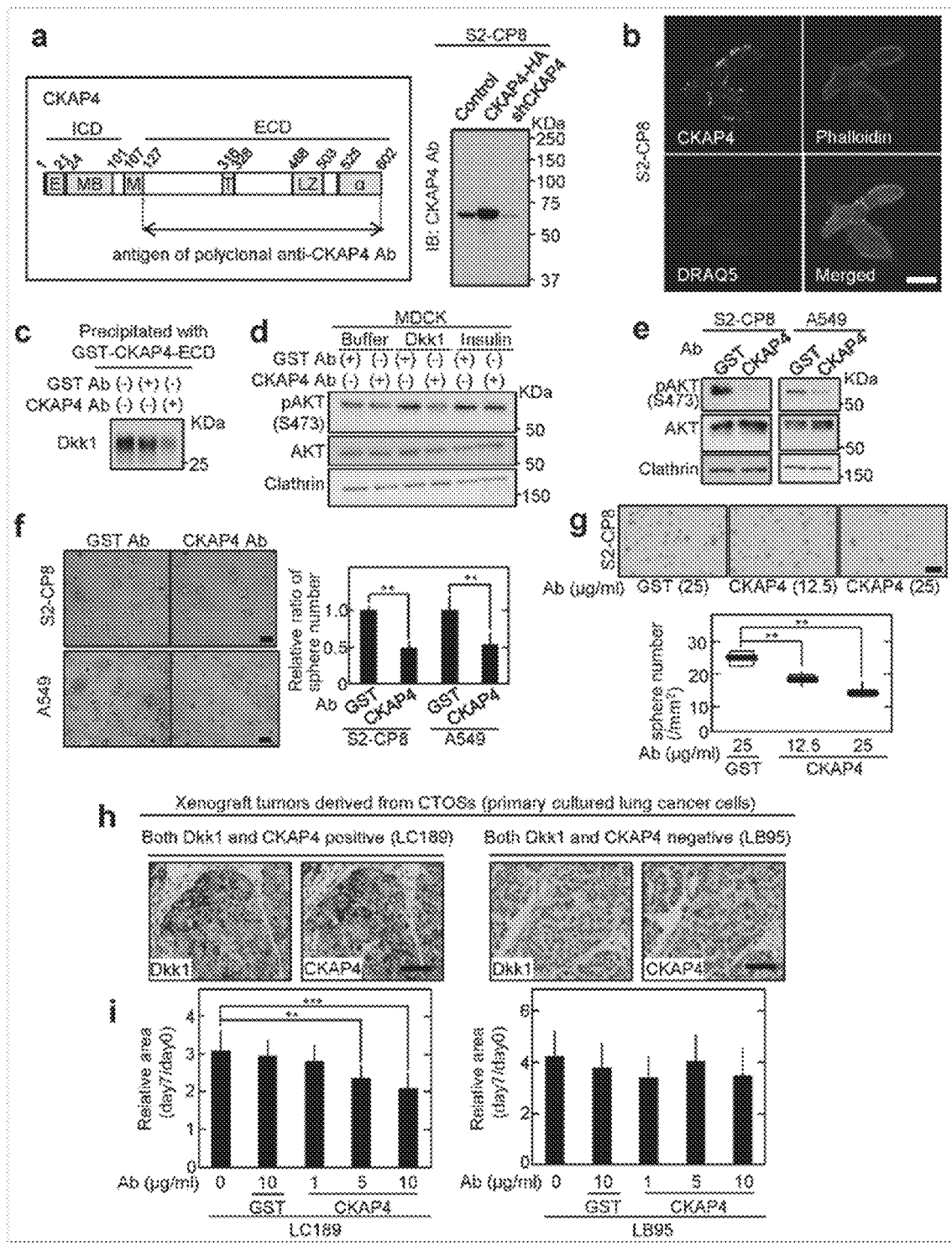
FIG. 12 (a) shows the schematic illustration of an epitope of a polyclonal anti-CKAP4 antibody (in the left panel) and the results of the detection of CKAP4 in a lysate of S2-CP8 cells (Control) or S2-CP8 cells expressing CKAP4 cDNA or CKAP4 shRNA (in the right panel).

In the left panel in FIG. 12 (a), an antigenic site in a polyclonal anti-CKAP4 antibody (CKAP4 pAb) is shown.

A lysate of S2-CP8 (control) or S2-CP8 cells expressing CKAP4 cDNA or CKAP4 shRNA was prepared, and the lysate was subjected to the detection of CKAP4 using an anti-CKAP4 antibody. The results are shown in the right panel in FIG. 12 (a). From the results, it was confirmed that the expression amount of CKAP4 in S2-CP8 cells expressing CKAP4 cDNA increased compared with that in the control and the expression amount of CKAP4 in S2-CP8 cells expressing CKAP4 shRNA was suppressed compared with the control. Consequently, it was demonstrated that the produced CKAP4 antibody acted property.

S2-CP8 cells proliferated on a collagen-coated glass slide was stained in an unfixed state with an anti-CKAP4 antibody (green). The actin cytoskeleton and nucleus of each of the cells were stained with phalloidin (red) and DRAQ5 DNA Dye (blue). The results are shown in FIG. 12 (b). From the results, it was confirmed that CKAP4 was expressed intensively on the cell membranes of S2-CP8 cells.

In 500 μl of NP40 buffer, 2 nM of GST-CKAP4-ECD was mixed with 20 nM of an anti-CKAP4 antibody (a rabbit anti-CKAP4 polyclonal antibody for which the antigenic site is an extracellular domain of CKAP4 shown in FIG. 12 (a)) or an anti-GST antibody. Subsequently, 2.5 nM of Dkk1 was added to the mixture, and the resultant mixture was incubated for 2 hours to produce precipitates. The precipitates were subjected to the detection of Dkk1 using an anti-Dkk1 antibody. The results are shown in FIG. 12 (c). From the results, it was confirmed that the binding between Dkk1 and CKAP4 was inhibited by the anti-CKAP4 antibody.

MDCK cells were treated with 1 nM of nocodazole for 24 hours, and then the cells were incubated together with 25 μg/ml of an anti-CKAP4 antibody or an anti-GST antibody for 4 hours. Subsequently, the cells were stimulated with 250 ng/ml of Dkk1 or 1 nM of insulin for 30 minutes in the presence of an anti-CKAP4 antibody or an anti-GST antibody. Subsequently, the cells were collected, then a lysate of the cells was prepared, and then the lysate was subjected to the detection of pAKT, AKT and clathrin using an anti-pAKT antibody, an anti-AKT antibody and an anti-clathrin antibody, respectively. The anti-GST antibody was used as a control, and clathrin was used as a loading control. The results are shown in FIG. 12 (d). From the results, it was confirmed that the anti-CKAP4 antibody suppressed the Dkk1-dependent activation of AKT but did not affect the insulin-dependent activity of AKT.

S2-CP8 cells or A549 cells were incubated together with 5 µg/ml of an anti-CKAP4 antibody or an anti-GST antibody for 4 hours. Subsequently, the cells were collected, then a lysate of the cells was prepared, and then the lysate was subjected to the detection of pAKT, AKT and clathrin using an anti-pAKT antibody, an anti-AKT antibody and an anti-clathrin antibody, respectively. The anti-GST antibody was used as a control, and clathrin was used as a loading control. The results are shown in FIG. 12 (e). From the results, it was confirmed that the anti-CKAP4 antibody suppressed the activation of AKT in cancer cells.

S2-CP8 cells ($2 \times 10^4$ cells) or A549 cells ($2 \times 10^4$ cells) were cultured three-dimensionally on a matrigel for 5 days in the presence of 5 µg/ml of an anti-GST antibody or 5 µg/ml of an anti-CKAP4 antibody, and the number of spheroids per one field was counted (in five fields). The anti-GST antibody was used as a control. The results are shown in FIG. 12 (f). ** represents P<0.01. From the results, it was confirmed that the number of spheroids was decreased by the action of the anti-CKAP4 antibody in S2-CP8 cells and A549 cells and therefore the anti-CKAP4 antibody was able to suppress the in vitro tumor formation ability of S2-CP8 cells and A549 cells.

S2-CP8 cells ($2 \times 10^4$ cells) were cultured on a matrigel three-dimensionally for 7 days in the presence of 25 µg/ml of an anti-GST antibody, 12.5 µg/ml of an anti-CKAP4 antibody or 25 µg/ml of an anti-CKAP4 antibody. The number of spheroids per 1 mm$^2$ was counted. The results are shown in FIG. 12 (g). In upper panels in FIG. 12 (g), the scale bar indicates 200 µm. In the lower panel in FIG. 12 (g), the average number was represented with a bold line, the box represents the $25^{th}$-$75^{th}$ percentile range, the error bars represent the $5^{th}$-$95^{th}$ percentile ranges, and ** represents P<0.01. From these results, it was confirmed that the anti-CKAP4 antibody was able to suppress the in vitro tumor formation ability of S2-CP8 cells.

Surgical specimens or pleural effusions were provided by two cancer patients from whom agreement was obtained in Center for Adult Diseases, Osaka. Each of the two samples (LC189 and LB95) was dispersed mechanically and enzymatically to collect 40 to 250 µm of a tissue section, and then the tissue section was subjected to floating culture using StemPro hESC (Invitrogen, Carlsbad, Calif.) to produce cancer tissue-originated spheroids (CTOSs). The CTOSs were transplanted into a NOD/scid mouse and the mouse was raised to form a xenograft tumor at the transplanted site in the mouse. Subsequently, a section produced from the xenograft tumor was immunostained with an anti-Dkk1 antibody or an anti-CKAP4 antibody and haematoxylin. The results are shown in FIG. 12 (h). From the results, it was confirmed that both of the expression amounts of Dkk1 and CKAP4 were high in the xenograft tumor of the sample LC189 while the expression of Dkk1 and CKAP4 was not observed in the xenograft tumor of the sample LB95.

Subsequently, CTOSs, which were isolated and cryopreserved again from the xenograft tumor obtained above, were thawed and then subjected to the following proliferation assay. More specifically, in the proliferation assay, the CTOSs were embedded in Matrigel Growth Factor Reduced (GFR) (BD Biosciences, Bedford, Mass.) and then cultured in a StemPro hESC medium supplemented with an anti-CKAP4 antibody or an anti-GST antibody at each of various concentrations for 7 days at 37° C. During the culture period, the area of the CTOSs was measured using Image J. (National Institutes of Health, Bethesda, Md.), and the ratio of the area of the CTOSs 7 days after the culture to that at the start point of the culture was determined (n=6 under the conditions where the antibody was not added; n=12 under the conditions where the antibody was added). The results are shown in FIG. 12 (i). In FIG. 12 (i),  represents P<0.01, and * represents P<0.001. From the results, the proliferation suppression effect was not observed even in the presence of the anti-CKAP4 antibody in the CTOSs of the sample LB95 in which the expression amounts of Dkk1 and CKAP4 were small while the proliferation suppression effect was observed significantly in the presence of the anti-CKAP4 antibody in the CTOSs of the sample LC189 in which the expression amounts of Dkk1 and CKAP4 were large.

Figure 13:
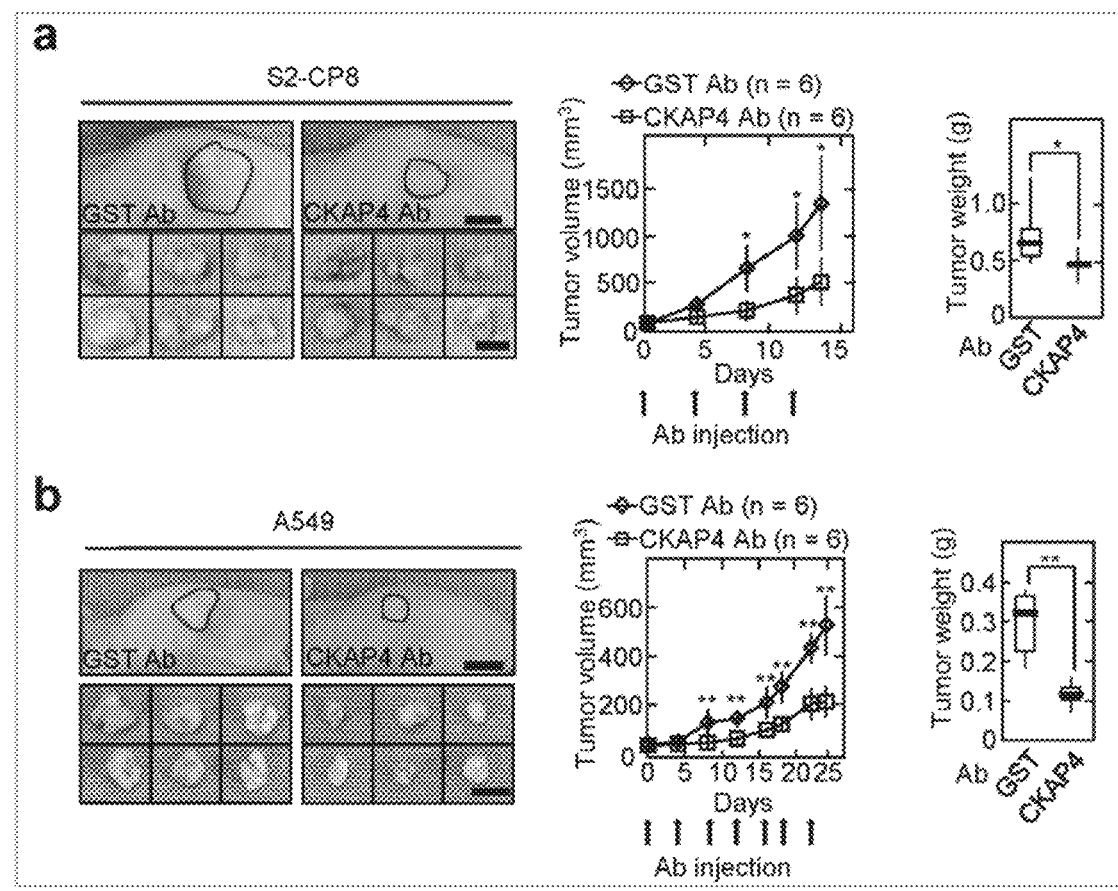
FIG. 13 (a) shows the results of the observation of nude mice which received the subcutaneous injection of S2-CP8 cells from above and the results of the observation of tumor xenografts extirpated from the nude mice (in the left panel) and the results of the measurement of the change in tumor volume of a tumor xenograft during the period of 14 days after the injection of an antibody and the final weight of the tumor xenograft (in the right panel).

Human pancreatic cancer cells (S2-CP8) ($5 \times 10^6$ cells) or human lung cancer cells (A549) ($5 \times 10^6$ cells) were injected subcutaneously to the back of each of nude mice. At the time point at which the average tumor size reached 50 mm$^3$, the nude mice were randomly divided into two groups. An anti-pCKAP4 antibody (150 µg/body) (n=6) or an anti-glutathione-S-transferase (GST) antibody (150 µg/body) (n=6) was injected to the peritoneal cavity for two weeks (on days 0, 4, 8, 12) for S2-CP8 cells and for 3.5 weeks (on days 0, 4, 9, 12, 16, 18, 22) for A549 cells at a frequency of twice per week. Tumor xenografts at the transplanted sites in the nude mice were analyzed after 14 days for S2-CP8 cells and after 25 days for A549 cells. The results for the human pancreatic cancer cells (S2-CP8) are shown in FIG. 13 (a), and the results for the human lung cancer cell (A549) ($5 \times 10^6$ cells) are shown in FIG. 13 (b). In the left panels in FIGS. 13 (a) and (b), the results of the observation of the nude mice from above after 14 days and 25 days are shown. In the lower left panels in FIGS. 13 (a) and (b), the results of the observation of the extirpated tumor xenografts are shown. In the upper left panels in FIGS. 13 (a) and (b), the broken lines represent the outline forms of the tumor xenografts. In the upper left panels and the lower left panels in FIGS. 13 (a) and (b), each of the scale bar indicates 10 mm. In the middle panels in FIGS. 13 (a) and (b), the results of the measurement of the volumes of the tumor xenografts are shown. In the right panels in FIGS. 13 (a) and (b), the results of the measurement of the weights of the tumor xenografts are shown. In the left panels in FIGS. 13 (a) and (b), each of the results is expressed in an average value±s. d. * represents P<0.05, and ** represents P<0.01. From the results, it was confirmed that the tumor formation ability of pancreatic cancer cells (S2-CP8) and lung cancer cells (A549) decreased by the administration of the anti-CKAP4 antibody.

2-9. Confirmation of Relationship Between Expression of CKAP4 in Exosome and Cancer Each of pancreatic cancer cells (SUIT-2 and S2-CP8), lung cancer cells (A549 and Calu-6), fetal normal kidney cells (X293T) and canine renal tubule-originated normal cells (MDCK) were cultured in a 10-cm dish until the cells reached a 80 to 90% confluent state, and a culture supernatant was collected. The culture supernatant was centrifuged under the conditions of 2,000×g and 10 minutes and then further centrifuged under the conditions of 10,000×g and 10 minutes to separate a cell debris. A collected supernatant was ultracentrifuged under the conditions of 4° C., 100,000×g and 3 hours to produce exosome pellets. The exosome pellets were washed with 1.2 ml of PBS, and the washed exosome pellets were subjected to the additional separation by ultracentrifugation under the conditions of 4° C., 100,000×g and 2 hours. Subsequently, a supernatant was discarded to collect exosomes, and the exosomes were lysed in Laemmli sample buffer. The lysate of the exosomes and a lysate of each of the cells were subjected to the detection of CKAP4, TSG101 and clathrin using an anti-CKAP4 antibody, an anti-TSG101 antibody and an anti-clathrin antibody, respectively.

Figure 14:
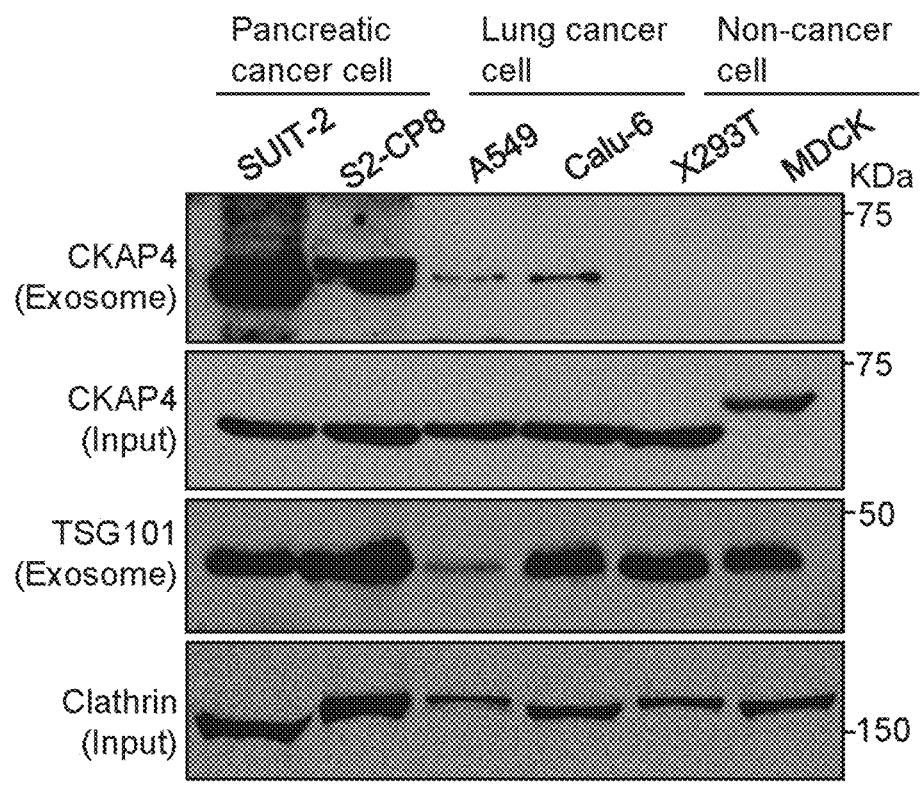
FIG. 14 shows the result of the detection of CKAP4 and TSG101 in exosomes collected from a cell culture of each of various cancer cell lines and normal cell lines and the detection of CKAP4 and clathrin in cell lysates (Input).

The results are shown in FIG. 14. From the results, CKAP4 was detected in the exosomes contained in the culture supernatants of the pancreatic cancer cells and lung cancer cells while CKAP4 was not detected in the exosomes contained in the culture supernatants of the normal cells. Namely, it was confirmed that it became possible to diagnose with respect to the presence or absence of the development of cancer by employing CKAP4 contained in exosomes as a measure.

What is claimed is:

1. A method for treating a cancer, comprising:
   identifying a cancer patient expressing cytoskeleton-associated protein 4 (CKAP4) and dickkopf-related protein 1 (Dkk1) in cancer cells,
   administering a therapeutically effective amount of a substance suppressing an expression or function of the CKAP4 and the Dkk1 to the cancer patient expressing the CKAP4 and the Dkk1.

2. The method according to claim 1, wherein the substance is at least one nucleic acid medicine selected from the group consisting of siRNA, shRNA, dsRNA, miRNA and an antisense nucleic acid against CKAP4.

3. The method according to claim 1, wherein the substance is an antibody binding specifically to CKAP4 or a fragment of the antibody.

4. The method according to claim 1, wherein the substance is applied for prevention of progression of a cancer.

5. The method according to claim 4, wherein the cancer is a lung cancer or a pancreatic cancer.

* * * * *

SEQUENCE LISTING

```
<160> NUMBER OF SEQ ID NOS: 9

<210> SEQ ID NO 1
<211> LENGTH: 602
<212> TYPE: PRT
<213> ORGANISM: Homo sapiens

<400> SEQUENCE: 1

Met Pro Ser Ala Lys Gln Arg Gly Ser Lys Gly Gly His Gly Ala Ala
1               5                   10                  15

Ser Pro Ser Glu Lys Gly Ala His Pro Ser Gly Gly Ala Asp Asp Val
                20                  25                  30

Ala Lys Lys Pro Pro Pro Ala Pro Gln Gln Pro Pro Pro Pro Pro Ala
            35                  40                  45

Pro His Pro Gln Gln His Pro Gln Gln His Pro Gln Asn Gln Ala His
        50                  55                  60

Gly Lys Gly Gly His Arg Gly Gly Gly Gly Gly Gly Lys Ser Ser
65                  70                  75                  80

Ser Ser Ser Ser Ala Ser Ala Ala Ala Ala Ala Ala Ala Ala Ser Ser
                85                  90                  95

Ser Ala Ser Cys Ser Arg Arg Leu Gly Arg Ala Leu Asn Phe Leu Phe
            100                 105                 110

Tyr Leu Ala Leu Val Ala Ala Ala Phe Ser Gly Trp Cys Val His
            115                 120                 125

His Val Leu Glu Glu Val Gln Gln Val Arg Arg Ser His Gln Asp Phe
        130                 135                 140

Ser Arg Gln Arg Glu Glu Leu Gly Gln Gly Leu Gln Gly Val Glu Gln
145                 150                 155                 160

Lys Val Gln Ser Leu Gln Ala Thr Phe Gly Thr Phe Glu Ser Ile Leu
                165                 170                 175

Arg Ser Ser Gln His Lys Gln Asp Leu Thr Glu Lys Ala Val Lys Gln
            180                 185                 190

Gly Glu Ser Glu Val Ser Arg Ile Ser Glu Val Leu Gln Lys Leu Gln
        195                 200                 205

Asn Glu Ile Leu Lys Asp Leu Ser Asp Gly Ile His Val Val Lys Asp
    210                 215                 220

Ala Arg Glu Arg Asp Phe Thr Ser Leu Glu Asn Thr Val Glu Glu Arg
225                 230                 235                 240

Leu Thr Glu Leu Thr Lys Ser Ile Asn Asp Asn Ile Ala Ile Phe Thr
                245                 250                 255

Glu Val Gln Lys Arg Ser Gln Lys Glu Ile Asn Asp Met Lys Ala Lys
            260                 265                 270

Val Ala Ser Leu Glu Glu Ser Glu Gly Asn Lys Gln Asp Leu Lys Ala
        275                 280                 285

Leu Lys Glu Ala Val Lys Glu Ile Gln Thr Ser Ala Lys Ser Arg Glu
    290                 295                 300
```

```
Trp Asp Met Glu Ala Leu Arg Ser Thr Leu Gln Thr Met Glu Ser Asp
305                 310                 315                 320

Ile Tyr Thr Glu Val Arg Glu Leu Val Ser Leu Lys Gln Glu Gln Gln
                325                 330                 335

Ala Phe Lys Glu Ala Ala Asp Thr Glu Arg Leu Ala Leu Gln Ala Leu
            340                 345                 350

Thr Glu Lys Leu Leu Arg Ser Glu Glu Ser Val Ser Arg Leu Pro Glu
        355                 360                 365

Glu Ile Arg Arg Leu Glu Glu Leu Arg Gln Leu Lys Ser Asp Ser
370                 375                 380

His Gly Pro Lys Glu Asp Gly Gly Phe Arg His Ser Glu Ala Phe Glu
385                 390                 395                 400

Ala Leu Gln Gln Lys Ser Gln Gly Leu Asp Ser Arg Leu Gln His Val
                405                 410                 415

Glu Asp Gly Val Leu Ser Met Gln Val Ala Ser Ala Arg Gln Thr Glu
            420                 425                 430

Ser Leu Glu Ser Leu Leu Ser Lys Ser Gln Glu His Glu Gln Arg Leu
        435                 440                 445

Ala Ala Leu Gln Gly Arg Leu Glu Gly Leu Gly Ser Ser Glu Ala Asp
450                 455                 460

Gln Asp Gly Leu Ala Ser Thr Val Arg Ser Leu Gly Glu Thr Gln Leu
465                 470                 475                 480

Val Leu Tyr Gly Asp Val Glu Leu Lys Arg Ser Val Gly Glu Leu
                485                 490                 495

Pro Ser Thr Val Glu Ser Leu Gln Lys Val Gln Glu Gln Val His Thr
                500                 505                 510

Leu Leu Ser Gln Asp Gln Ala Gln Ala Ala Arg Leu Pro Pro Gln Asp
        515                 520                 525

Phe Leu Asp Arg Leu Ser Ser Leu Asp Asn Leu Lys Ala Ser Val Ser
530                 535                 540

Gln Val Glu Ala Asp Leu Lys Met Leu Arg Thr Ala Val Asp Ser Leu
545                 550                 555                 560

Val Ala Tyr Ser Val Lys Ile Glu Thr Asn Glu Asn Asn Leu Glu Ser
                565                 570                 575

Ala Lys Gly Leu Leu Asp Asp Leu Arg Asn Asp Leu Asp Arg Leu Phe
            580                 585                 590

Val Lys Val Glu Lys Ile His Glu Lys Val
        595                 600

<210> SEQ ID NO 2
<211> LENGTH: 1809
<212> TYPE: DNA
<213> ORGANISM: Homo sapiens

<400> SEQUENCE: 2
atgccctcgg ccaaacaaag gggctccaag ggcggccacg gcgccgcgag ccctcggag      60 aagggtgccc acccgtcggg cggcgcggat gacgtggcga agaagccgcc gccggcgccg     120
cagcagccgc cgccgccgcc cgcgccgcac ccgcagcagc accgcagca gcacccgcag      180 aaccaggcgc acggcaaggg cggccaccgc ggcggcggcg gcggcggcgg caagtcctcc     240
tcctcctcct ccgcctccgc cgccgctgcc gccgccgccg cctcgtcctc ggcgtcctgc     300
tcgcgcaggc tcggcagggc gctcaacttt ctcttctacc tcgccctggt ggcggcggcc     360
gctttctcgg gctggtgcgt ccaccacgtc ctggaggagg tccagcaggt ccggcgcagc     420
```

```
caccaggact tctcccggca gagggaggag ctgggccagg gcttgcaggg cgtcgagcag    480
aaggtgcagt ctttgcaagc cacatttgga acttttgagt ccatcttgag aagctcccaa    540
cataaacaag acctcacaga gaaagctgtg aagcaagggg agagtgaggt cagccggatc    600
agcgaagtgc tgcagaaact ccagaatgag attctcaaag acctctcgga tgggatccat    660
gtggtgaagg acgcccggga gcgggacttc acgtccctgg agaacacggt ggaggagcgg    720
ctgacggagc tcaccaaatc catcaacgac aacatcgcca tcttcacaga agtccagaag    780
aggagccaga aggagatcaa tgacatgaag gcaaaggttg cctccctgga agaatctgag    840
gggaacaagc aggatttgaa agccttaaag gaagctgtga aggagataca gacctcagcc    900
aagtccagag agtgggacat ggaggccctg agaagtaccc ttcagactat ggagtctgac    960
atctacaccg aggtccgcga gctggtgagc ctcaagcagg agcagcaggc tttcaaggag    1020
gcggccgaca cggagcggct cgccctgcag gccctcacgg agaagcttct caggtctgag    1080
gagtccgtct cccgcctccc ggaggagatc cggagactgg aggaagagct ccgccagctg    1140
aagtccgatt cccacgggcc gaaggaggac ggaggcttca cactcggaa agcctttgag    1200 gcactccagc aaaagagtca gggactggac tccaggctcc agcacgtgga ggatggggtg    1260
ctctccatgc aggtggcttc tgcgcgccag accgagagcc tggagtccct cctgtccaag    1320
agccaggagc acgagcagcg cctggccgcc ctgcaggggc cctggaagg cctcgggtcc    1380 tcagaggcag accaggatgg cctggccagc acggtgagga gctgggcga acccagctg    1440 gtgctctacg gtgacgtgga ggagctgaag aggagtgtgg gcgagctccc cagcaccgtg    1500
gaatcactcc agaaggtgca ggagcaggtg cacacgctgc tcagtcagga ccaagcccag    1560
gccgcccgtc tgcctcctca ggacttcctg gacagacttt cttctctaga aacctgaaa    1620 gcctcagtca gccaagtgga ggcggacttg aaaatgctca ggactgctgt ggacagtttg    1680
gttgcatact cggtcaaaat agaaaccaac gagaacaatc tggaatcagc caagggttta    1740
ctagatgacc tgaggaatga tctggatagg ttgtttgtga agtggagaa gattcacgaa    1800 aaggtctaa                                                           1809
```

<210> SEQ ID NO 3
<211> LENGTH: 801
<212> TYPE: DNA
<213> ORGANISM: Homo sapiens

<400> SEQUENCE: 3

```
atgatggctc tgggcgcagc gggagctacc cgggtctttg tcgcgatggt agcggcggct    60
ctcggcggcc accctctgct gggagtgagc gccaccttga actcggttct caattccaac    120
gctatcaaga acctgccccc accgctgggc ggcgctgcgg ggcacccagg ctctgcagtc    180
agcgccgcgc cgggaatcct gtacccgggc gggaataagt accagaccat tgacaactac    240
cagccgtacc cgtgcgcaga ggacgaggag tgcggcactg atgagtactg cgctagtccc    300
acccgcggag gggacgcagg cgtgcaaatc tgtctcgcct gcaggaagcg ccgaaaacgc    360
tgcatgcgtc acgctatgtg ctgccccggg aattactgca aaaatggaat atgtgtgtct    420
tctgatcaaa atcatttccg aggagaaatt gaggaaacca tcactgaaag ctttggtaat    480
gatcatagca ccttggatgg gtattccaga agaaccacct tgtcttcaaa aatgtatcac    540
accaaaggac aagaaggttc tgtttgtctc cggtcatcag actgtgcctc aggattgtgt    600
tgtgctagac acttctggtc caagatctgt aaacctgtcc tgaaagaagg tcaagtgtgt    660
accaagcata ggagaaaagg ctctcatgga ctagaaatat ccagcgttg ttactgtgga    720
```

```
gaaggtctgt cttgccggat acagaaagat caccatcaag ccagtaattc ttctaggctt    780
cacacttgtc agagacacta a                                              801
```

<210> SEQ ID NO 4
<211> LENGTH: 909
<212> TYPE: DNA
<213> ORGANISM: Artificial Sequence
<220> FEATURE:
<223> OTHER INFORMATION: Base sequence of human DKK1-FLAG-GPI

<400> SEQUENCE: 4

```
atgatggctc tgggcgcagc gggagctacc cgggtctttg tcgcgatggt agcggcggct     60
ctcggcggcc accctctgct gggagtgagc gccaccttga actcggttct caattccaac   120
gctatcaaga acctgccccc accgctgggc ggcgctgcgg ggcacccagg ctctgcagtc   180
agcgccgcgc cgggaatcct gtacccgggc gggaataagt accagaccat tgacaactac   240
cagccgtacc cgtgcgcaga ggacgaggag tgcggcactg atgagtactg cgctagtccc   300
acccgcggag gggacgcagg cgtgcaaatc tgtctcgcct gcaggaagcg ccgaaaacgc   360
tgcatgcgtc acgctatgtg ctgccccggg aattactgca aaaatggaat atgtgtgtct   420
tctgatcaaa atcatttccg aggagaaatt gaggaaacca tcactgaaag ctttggtaat   480
gatcatagca ccttggatgg gtattccaga agaaccacct tgtcttcaaa aatgtatcac   540
accaaaggac aagaaggttc tgtttgtctc cggtcatcag actgtgcctc aggattgtgt   600
tgtgctagac acttctggtc caagatctgt aaacctgtcc tgaaagaagg tcaagtgtgt   660
accaagcata ggagaaaagg ctctcatgga ctagaaatat ccagcgttg ttactgtgga   720 gaaggtctgt cttgccggat acagaaagat caccatcaag ccagtaattc ttctaggctt   780
cacacttgtc agagacacga ctacaaggac gacgatgaca agagtgctgg tgtccgtcct   840
ggggcacagg cctacctcct cactgtcttc tgcatcttgt cctggttat gcagagagag   900 tggagataa                                                           909
```

<210> SEQ ID NO 5
<211> LENGTH: 19
<212> TYPE: DNA
<213> ORGANISM: Homo sapiens

<400> SEQUENCE: 5

```
cagtcgcgtt tgcgactgg                                                 19
```

<210> SEQ ID NO 6
<211> LENGTH: 19
<212> TYPE: DNA
<213> ORGANISM: Canis lupus familiaris

<400> SEQUENCE: 6

```
gcagaaggtg cagtctctt                                                 19
```

<210> SEQ ID NO 7
<211> LENGTH: 19
<212> TYPE: DNA
<213> ORGANISM: Homo sapiens

<400> SEQUENCE: 7

```
gtgcgttgct agtaccaac                                                 19
```

<210> SEQ ID NO 8

```
<211> LENGTH: 19
<212> TYPE: DNA
<213> ORGANISM: Homo sapiens

<400> SEQUENCE: 8
gggtttcttg gaatgacga                                                   19

<210> SEQ ID NO 9
<211> LENGTH: 19
<212> TYPE: DNA
<213> ORGANISM: Homo sapiens

<400> SEQUENCE: 9
gcagattaac ctcagaaat                                                   19
```